US010398364B2

(12) United States Patent
Cheng

(10) Patent No.: US 10,398,364 B2
(45) Date of Patent: Sep. 3, 2019

(54) METHOD AND DEVICE FOR MEASURING VENOUS BLOOD OXYGENATION

(71) Applicant: MESPERE LIFESCIENCES INC., Waterloo (CA)

(72) Inventor: Xuefeng Cheng, Waterloo (CA)

(73) Assignee: Mespere Lifesciences Inc., Waterloo, Ontario (CA)

( * ) Notice: Subject to any disclaimer, the term of this patent is extended or adjusted under 35 U.S.C. 154(b) by 723 days.

(21) Appl. No.: 14/767,698

(22) PCT Filed: Feb. 13, 2014

(86) PCT No.: PCT/CA2014/000106
§ 371 (c)(1),
(2) Date: Aug. 13, 2015

(87) PCT Pub. No.: WO2014/124520
PCT Pub. Date: Aug. 21, 2014

(65) Prior Publication Data
US 2015/0351675 A1 Dec. 10, 2015

Related U.S. Application Data

(63) Continuation-in-part of application No. 13/765,843, filed on Feb. 13, 2013, now Pat. No. 8,918,153.

(51) Int. Cl.
*A61B 5/00* (2006.01)
*A61B 5/1455* (2006.01)
(Continued)

(52) U.S. Cl.
CPC ........ *A61B 5/14552* (2013.01); *A61B 5/0295* (2013.01); *A61B 5/02116* (2013.01);
(Continued)

(58) Field of Classification Search
CPC ... A61B 5/0059; A61B 5/145; A61B 5/14542; A61B 5/1455; A61B 5/14551;
(Continued)

(56) References Cited

U.S. PATENT DOCUMENTS 3,413,970 A * 12/1968 Rockwell ........... A61B 5/02152
600/487
4,321,930 A 3/1982 Jobsis et al.
(Continued)

FOREIGN PATENT DOCUMENTS

CA 2494030 2/2004
CA 2815643 7/2012
(Continued)

OTHER PUBLICATIONS

Seth, R., Magner, P., Matzinger, F. and Van Walraven, C. (2002), How Far is the Sternal Angle from the Mid-right Atrium?. Journal of General Internal Medicine, 17: 861-865. doi: 10.1046/j. 1525-1497.2002.20101.x.
(Continued)

*Primary Examiner* — Eric F Winakur
*Assistant Examiner* — Chu Chuan Liu
(74) *Attorney, Agent, or Firm* — Gowling WLG (Canada) LLP

(57) ABSTRACT

A device for non-invasively measuring at least one parameter of a cardiac blood vessel in a patient comprises at least one light source that directs light at a tissue site on the patient; at least one photodetector adapted to receive light emitted by the light source and generate an output based on the received light, the output of said photodetector being correlated with a parameter of the blood vessel; and at least one probe for facilitating delivery of light from the light source to the tissue site, and receipt of light by the photodetector. The device may include a height sensor to adapt it (Continued)

for use to determine central venous pressure, or the configuration of light source(s) and photodetector(s) may be adapted to permit the device to provide attenuation correction in the determination of venous blood oxygenation.

6 Claims, 21 Drawing Sheets

(51) Int. Cl.
*A61B 5/0295* (2006.01)
*A61B 5/024* (2006.01)
*A61B 5/021* (2006.01)
A61B 5/0205 (2006.01)
A61B 5/026 (2006.01)
A61B 5/029 (2006.01)

(52) U.S. Cl.
CPC ...... *A61B 5/02141* (2013.01); *A61B 5/02427* (2013.01); *A61B 5/02433* (2013.01); *A61B 5/6822* (2013.01); *A61B 5/0205* (2013.01); *A61B 5/029* (2013.01); *A61B 5/0261* (2013.01); *A61B 5/14551* (2013.01); *A61B 2560/0261* (2013.01); *A61B 2562/0233* (2013.01); *A61B 2562/046* (2013.01)

(58) Field of Classification Search
CPC ....... A61B 5/14552; A61B 5/72; A61B 5/021; A61B 5/02116; A61B 5/6822; A61B 5/0205; A61B 5/0261; A61B 5/029
See application file for complete search history.

(56) References Cited

U.S. PATENT DOCUMENTS

| | | | | |
|---|---|---|---|---|
| 4,397,099 | A | * | 8/1983 | Gaucher ............ G01C 5/04 33/367 |
| 5,069,214 | A | | 12/1991 | Samaras et al. |
| 5,101,825 | A | | 4/1992 | Gravenstein et al. |
| 5,269,310 | A | | 12/1993 | Jones et al. |
| 5,277,181 | A | * | 1/1994 | Mendelson ........ A61B 5/14551 356/41 |
| 5,524,617 | A | * | 6/1996 | Mannheimer ...... A61B 5/14551 356/41 |
| 5,788,641 | A | | 8/1998 | Policastro et al. |
| 6,078,833 | A | | 6/2000 | Hueber et al. |
| 6,151,518 | A | | 11/2000 | Hayashi |
| 6,334,065 | B1 | | 12/2001 | Al-Ali et al. |
| 6,496,711 | B1 | | 12/2002 | Athan et al. |
| 6,537,225 | B1 | * | 3/2003 | Mills ................ A61B 5/14552 600/323 |
| 6,587,703 | B2 | | 6/2003 | Cheng |
| 6,801,648 | B2 | | 10/2004 | Cheng et al. |
| 7,072,701 | B2 | * | 7/2006 | Chen ................ A61B 5/14553 600/331 |
| 7,725,187 | B1 | | 5/2010 | Nabutovsky et al. |
| 7,738,935 | B1 | | 6/2010 | Turcott |
| 8,417,306 | B2 | | 4/2013 | Cheng |
| 8,463,348 | B2 | | 6/2013 | Cheng |
| 8,788,005 | B1 | | 7/2014 | Cheng |
| 8,918,153 | B2 | | 12/2014 | Cheng |
| 2006/0189872 | A1 | | 8/2006 | Arnold |
| 2006/0224053 | A1 | | 10/2006 | Black et al. |
| 2006/0253007 | A1 | | 11/2006 | Cheng |
| 2007/0167783 | A1 | | 11/2007 | Vikomerson |
| 2008/0316488 | A1 | * | 12/2008 | Mao ................ A61B 5/14552 356/432 |
| 2009/0163775 | A1 | * | 6/2009 | Barrett ............. A61B 5/14553 600/301 |
| 2010/0198027 | A1 | | 8/2010 | Dixon |
| 2010/0222658 | A1 | | 9/2010 | Cheng |
| 2012/0209095 | A1 | | 8/2012 | Huiku |

FOREIGN PATENT DOCUMENTS

| | | |
|---|---|---|
| CN | 2050155 | 12/1989 |
| CN | 1333001 | 1/2002 |
| CN | 101554328 | 10/2009 |
| CN | 201628542 | 11/2010 |
| EP | 2120689 | 11/2009 |
| JP | 11-244268 | 9/1999 |
| JP | 2003-532107 | 10/2003 |
| JP | 2005-533609 | 11/2005 |
| WO | 2001/084107 | 11/2001 |
| WO | 2004/010844 | 2/2004 |
| WO | 2006/097910 | 9/2006 |
| WO | 2006/124696 | 11/2006 |
| WO | 2007/012197 | 2/2007 |
| WO | 2007/097702 | 8/2007 |
| WO | 2008/098353 | 8/2008 |
| WO | 2008/134813 A1 | 11/2008 |

OTHER PUBLICATIONS

Garg et al, "Jugular Venous Pulse: An Appraisal", Journal, Indian Academy of Clinical Medicine, vol. 1, No. 3, Oct.-Dec. 2000.
O'Rourke, R.A. and Others, General Examination of the Patient, Hurst's, The Heart, Eighth Edition, pp. 238-242.
Conway "Clinical Assessment of Cardiac Output", Eur. Heart J. 11, 148-150 (1990).
Linton et al., "Advances in Non-invasive Cardiac Output Monitoring", Annals of Cardiac Anaesthesia, 2002, vol. 5, p. 141-148.
Conway, "Thermodilution Method for Measuring Cardiac Output", Europ. Heart J. 11 (Suppl 1), 17-20, 1990.
Lund-Johansen, "The Dye Dilution Method for Measurement of Cardiac Output", Europ. Heart J. 11 (Suppl 1), 6-12 (1990)).
deLeeuw and Birkenhager ("Some comments of the usefulness of measuring cardiac output by dye dilution", Europ. Heart J. 11 (Supple 1), 13-16 (1990)).
Keinanen, "Continuous Measurement of Cardiac Output by the Fick Principle: Clinical Validation in Intensive Care", Critical Care Med 20(3), 360-365 (1992).
Doi et al., "Frequently Repeated Fick Cardiac Output Measurements During Anesthesia", J. Clin. Monit. 6, 107-112 (1990).
Botero, et al., "Measurement of cardiac output before and after cardiopulmonary bypass: Comparison among aortic transit-time ultrasound, thermodilution, and noninvasive partial CO2 rebreathing", J. Cardiothoracic Vasc. Anesth. 18 (5) 563-572 (2004).
Nilsson et al "Lack of Agreement Between Thermodilution and CO2-rebreathing Cardiac Output" Acta Anaesthesiol Scan 2001; 45:680.
Schmidlin et al, "Transoesophageal Echocardiography in Cardiac and Vascular Surgery: Implications and Observer Variability", Brit. J. Anaesth. 86(4), 497-505 (2001).
Manning et al. "Validity and Reliability of Diastolic Pulse Contour Analysis (Windkessel model) in Humans", Hypertension. 2002 May 2002; 39(5):963-968.
Rauch et al., "Pulse Contour Analysis Versus Thermodilution in Cardiac Surgery", Acta Anaesthesiol Scand 2002:46:424.
Linton et al., "Estimation of Changes in Cardiac Output from Arterial Blood Pressure Waveform in the Upper Limb", Br J Anaesth 2001; 86:486.
Jansen et al., "A Comparison of Cardiac Output Derived from the Arterial Pressure Wave Against Thermodilution in cardiac Surgery Patients" BR J Anaesth 2001; 87:212.
Jansen et al. "An Adequate Strategy for the Thermodilution Technique in Patients During Mechanical Ventilation", Intensive Care Med 1990: 16-422.
http://depts.washington.edu/physdx/neck/tech2.html.
Colquhoun et al. Non-invasive estimation of jugular venous oxygen saturation: a comparison between near infrared spectroscopy and transcutaneous venous oximetry. Journal of Clinical Monitoring and Computing (2012) 26:91-98.

* cited by examiner

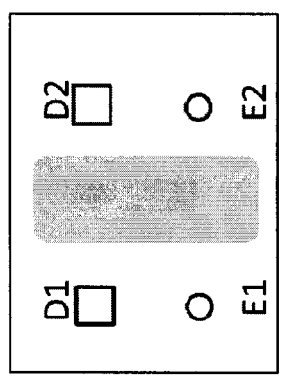
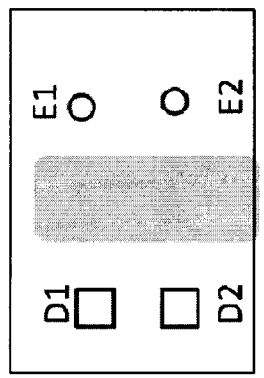
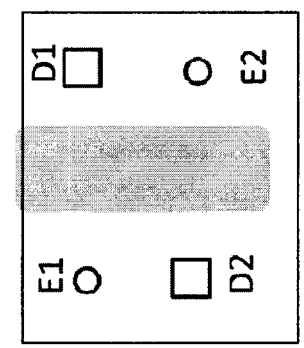
Figure 19 continued

METHOD AND DEVICE FOR MEASURING VENOUS BLOOD OXYGENATION

FIELD OF THE INVENTION

The present invention is related to techniques for monitoring vital functions of the human body, including cardiac functions such as cardiac output and central venous blood oxygenation. It relates, in particular, to an optical method and device for the non-invasive and continuous monitoring of cardiac parameters such as blood flow, blood volume and blood oxygen saturation.

BACKGROUND OF THE INVENTION

The evaluation of jugular venous pulse has been an integral part of cardiovascular examination and has important clinical diagnostic values [1-2]. Jugular venous pulse is produced by the changes in blood flow and pressure in central veins caused by right atrial and ventricular filling and contraction. The two main objectives of the bedside examination of jugular vein pulse include the estimation of central venous pressure and the inspection of the waveform. Because of its more direct route to the right atrium, the right internal jugular vein is superior for the purpose. Based upon these measurements, physicians can access hemodynamic events in the right atrium and thus diagnose heart diseases and abnormalities. For example, the most common cause of elevated jugular venous pressure is an increase in right ventricular pressure such as occurs in patients with pulmonary stenosis, pulmonary hypertension, or right ventricular failure secondary to right ventricular infarction. The venous pressure also is elevated when obstruction to right ventricular inflow occurs, such as with tricuspid stenosis or right atrial myxoma, or when constructive pericardial disease impedes right ventricular inflow. It may also result from vena caval obstruction and, at times, an increased blood volume. Patients with obstructive pulmonary disease may have an elevated venous pressure only during expiration.

The conventional technique for measuring venous pulse and waveform has been described in the literature [3]. The patient is examined at the optimum degree of trunk elevation for visualization of venous pulsations. The venous pressure is measured by a ruler as the vertical distance from the top of the oscillating venous column, to the level of the sternal angle plus vertical distance to the right atrium Due to the fact that the venous pulse is in generally very small, and due to complications with patients, this method is challenging for physicians to use and provides approximate values only.

Cardiac output is defined as the volume of blood circulated per minute. It is equal to the heart rate multiplied by the stroke volume (the amount ejected by the heart with each contraction). Cardiac output is of central importance in the monitoring of cardiovascular health [4]. Accurate clinical assessment of circulatory status is particularly desirable in critically ill patients in the ICU and patients undergoing cardiac, thoracic, or vascular interventions, and has proven valuable in long term follow-up of outpatient therapies. As a patient's hemodynamic status may change rapidly, continuous monitoring of cardiac output will provide information that allows rapid adjustment of therapy. Measurements of cardiac output and blood pressure can also be used to calculate peripheral resistance.

Jansen (J. R. C. Jansen, "Novel methods of invasive/non-invasive cardiac output monitoring", Abstracts of the 7th annual meeting of the European Society for Intravenous Anesthesia, Lisbon 2004) describes eight desirable characteristics for cardiac output monitoring techniques; accuracy, reproducibility or precision, fast response time, operator independency, ease of use, continuous use, cost effectiveness, and no increased mortality and morbidity.

Pulmonary artery catheter (PAC) thermodilution method is generally accepted as the clinical standard for monitoring cardiac output, to which all other methods are compared as discussed by Conway and Lund-Johansen [6]. As this technology is highly invasive, complicated, and expensive, many new methods have been developed in an attempt to replace it, but none have so far gained acceptance. A recent review of the various techniques for measuring cardiac output is given in Linton and Gilon [5]. This article lists both non/minimally invasive and invasive methods and compares the advantages and disadvantages of each. A brief description of some of these techniques follows.

Indicator Dilution Techniques.

There are several indicator dilution techniques including transpulmonary thermodilution (also known as PiCCO technology, Pulsion Medical Technologies of Munich, Germany), transpulmonary lithium dilution method (LiDCO Group plc of London, UK), PAC based thermo-dilution and other methods (Vigilance, Baxter; Opti-Q, Abbott; and TruCCOMS, AorTech). Application of such techniques assumes three major conditions, namely, complete mixing of blood and indicator, no loss of indicator between place of injection and place of detection, and constant blood flow. The errors associated with indicator dilution techniques are primarily related to the violation of these conditions, as discussed by Lund-Johansen [7-8].

Fick Principle.

The direct oxygen Fick approach is currently the standard reference technique for cardiac output measurement as discussed by Keinanen et al [9-10]. It is generally considered the most accurate method currently available. The NICO (Novametrix) system is a non-invasive device that applies Fick's principle and relies solely on airway gas measurement as described by Botero et al [11]. This method shows a lack of agreement between thermodilution and $CO_2$-rebreathing cardiac output as described in Nielsson et al [12], due to unknown ventilation/perfusion inequality in patients.

Bio-Impedance and Conduction Techniques.

The bio-impedance method was developed as a simple, low-cost method that gives information about the cardiovascular system and/or (de)-hydration status of the body in a non-invasive way. Over the years, a diversity of thoracic impedance measurement systems have also been developed. These systems determine CO on a beat-to-beat time basis. Studies have been reported with mostly poor results, but in some exceptional cases, there was good correlation with a reference method. Many of these studies refer to the poor physical principles of the thoracic impedance method as described in Patterson "Fundamentals of impedance cardiography", IEEE Engineering in Medicine and Biology 1989; 35 to explain the discrepancies.

Echo Doppler Ultrasound.

This technique uses ultrasound and the Doppler Effect to measure cardiac output. The blood velocity through the aorta causes a 'Doppler shift' in the frequency of the returning ultrasound waves. Echo-Doppler probes positioned inside the esophagus with their echo window on the thoracic aorta may be used for measuring aortic flow velocity, as discussed by Schmidlin et al [13]. Aortic cross sectional area is assumed in devices such as the CardioQ, made by Deltex Medical PLC, Chichester, UK, or measured simultaneously as, for example, in the HemoSonic device made by Arrow International. With these minimally invasive techniques what is measured is aortic blood flow, not cardiac output. A fixed relationship between aortic blood flow and cardiac output is assumed. Echo-Doppler ultrasound requires an above average level of skill on the part of the operator of the ultrasound machine to get accurate reliable results.

Arterial Pulse Contour Analysis.

The estimation of cardiac output based on pulse contour analysis is an indirect method, since cardiac output is not measured directly but is computed from a pressure pulsation on the basis of a criterion or model [14-17]. Three pulse contour methods are currently available; PiCCO (Pulsion), PulseCO (LiDCO) and Modelflow (TNO/BMI). All three of these pulse contour methods use an invasively measured arterial blood pressure and they need to be calibrated. PiCCO is calibrated by transpulmonary thermodilution, LiDCO by transpulmonary lithium dilution and Modelflow by the mean of 3 or 4 conventional thermodilution measurements equally spread over the ventilatory cycle.

Near infrared spectroscopy has been used to non-invasively measure various physiological properties in animal and human subjects. The basic principle underlying near infrared spectroscopy is that a physiological medium such as tissues includes a variety of light-absorbing (chromophores) and light-scattering substances which can interact with transmitted low energy near infrared photons. For example, deoxygenated and oxygenated hemoglobins in human blood are the most dominant chromophores in the spectrum range of 400 nm to 1000 nm. Therefore, diffuse optical spectroscopy has been applied to non-invasively measure oxygen levels in the physiological medium in terms of tissue hemoglobin oxygen saturation. Technical background for diffuse optical spectroscopy has been discussed in, e.g., Neuman, M. R., Pulse Oximetry: Physical Principles, Technical Realization and Present Limitations, @ Adv. Exp. Med. Biol., vol. 220, p. 135-144, 1987 and Severinghaus, J. W., History and Recent Developments in Pulse Oximetry, @ Scan. J. Clin. and Lab. Investigations, vol. 53, p. 105-111, 1993.

Because of the highly scattering nature of tissue to the visible and near infrared light (400 nm-1000 nm), it is difficult to apply diffuse optical spectroscopy non-invasively to select blood vessels within a tissue to calculate blood oxygenation. Thus, diffuse optical spectroscopy has only been used to measure the combined or average oxygenation of blood from arteries, veins, and capillaries within a tissue medium. However, in many clinical applications, it is desirable to know the blood oxygenation of particular blood vessels. To do so, various invasive methods have been developed which involve the use of catheters that must be inserted into a targeted blood vessel to make the measurement.

None of the above-mentioned techniques of measuring cardiac output combines all of the eight "Jansen" criteria mentioned above and, thus, none can displace the conventional thermodilution technique as described by Jansen et al [18]. Although highly invasive, complicated and expensive, the conventional thermodilution method remains the method of choice for measuring cardiac output. Given the foregoing, it would be highly desirable to develop a non-invasive method for real-time monitoring of cardiac output in a clinical setting which is accurate, reliable, cost effective and easy to use.

SUMMARY OF THE INVENTION

The present invention provides a device, system and method by which cardiac parameters can be continuously monitored in a non-invasive manner by the optical measure of venous blood flow, venous blood pressure and blood content including oxygenation.

In, particular, one aspect of the invention, a device for non-invasively measuring venous blood oxygenation is provided comprising:
one or more light sources to emit at least two different wavelengths of light, wavelength 1 and wavelength 2, in the 400 nm to 1000 nm wavelength range;
one or more photodetectors to receive wavelength 1 and wavelength 2 of light emitted by the one or more light sources and translate said light into a recordable output wherein said light is reflected from or transmitted through tissue of the patient, wherein the distance between the light source and photodetector that emit and receive light of wavelength 1 is different the distance between light source and photodetector that emit and receive light of wavelength 2; and
at least one probe which facilitates delivery of light from the light source to an external tissue site on the patient in the proximity of the jugular vein and receipt of light reflected from or transmitted through said patient site by the photodetector.

In another aspect of the invention, a method for determining venous blood oxygenation in a patient is provided comprising the steps of:
directing light from one or more light sources having first and second wavelengths which are different, selected from a wavelength in the range of 400-1000 nm, at the external tissue site on the patient in the proximity of the internal or external jugular vein;
detecting light reflected from the tissue or transmitted through the tissue at the first and second wavelengths and translating the detected light into an output current for the first and second wavelengths using one or more photodetectors, wherein the distance between the light source and photodetector that emit and receive light of wavelength 1 is different from the distance between light source and photodetector that emit and receive light of wavelength 2; and
determining using a processor the attenuation correction at the external tissue site on the patient based on the optical attenuation at each wavelength, and the venous blood oxygenation by applying the attenuation correction to the measured venous blood oxygenation.

In another aspect of the invention, a device is provided comprising:
at least one light source adapted to emit light in the 400 nm to 1000 nm wavelength range;
at least one photodetector adapted to receive light emitted by the light source and translate said light into a recordable output wherein said light is reflected from or transmitted through tissue of the patient;
at least one probe which facilitates delivery of light from the light source to an external tissue site on the patient in the proximity of the jugular vein and receipt of light reflected from or transmitted through said patient site by the photodetector; and
a height sensor for mounting on the probe, said height sensor comprising a pressure sensor connected to a reference patch via a tube, wherein the tube is suitable to contain a liquid.

These and other aspects of the present invention will become apparent by reference to the detailed description that follows, and the drawings in which:

DETAILED DESCRIPTION OF THE INVENTION

Figure 1:
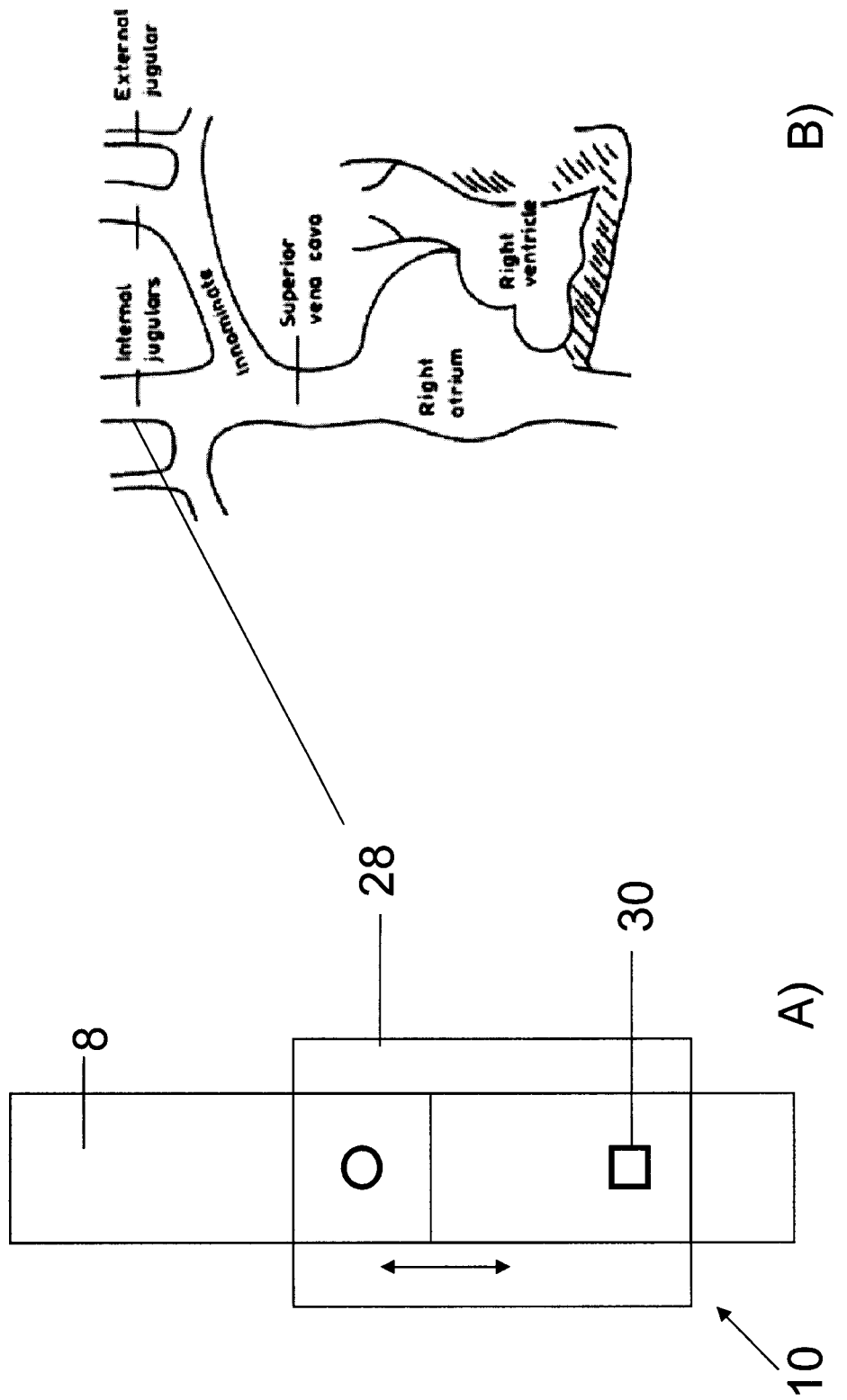
FIG. 1 illustrates a top view of a device (A) for monitoring cardiac output in accordance with an aspect of the invention and placement of the device relative to cardiac vessels (B)
Figure 2:
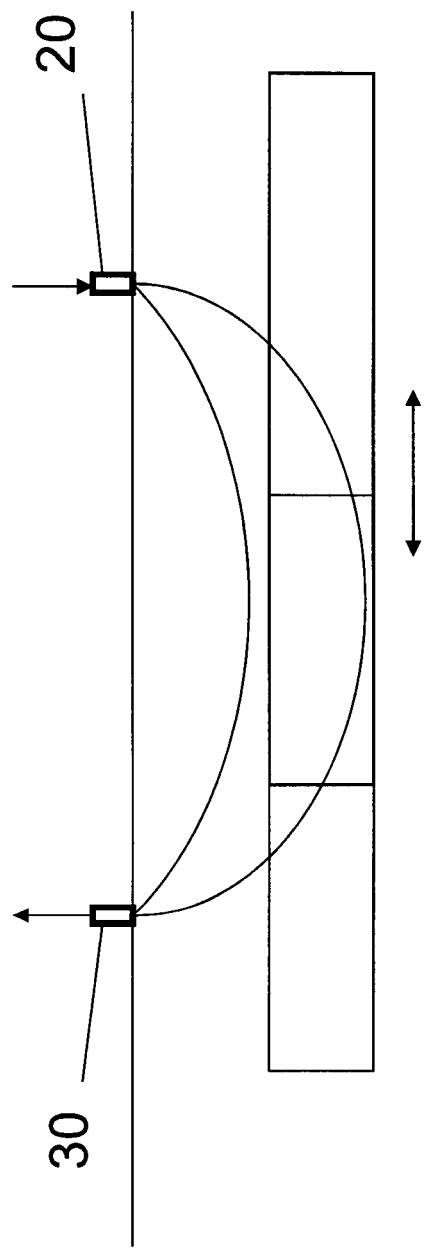
FIG. 2 illustrates a side view of a device as in FIG. 1.
Figure 3:
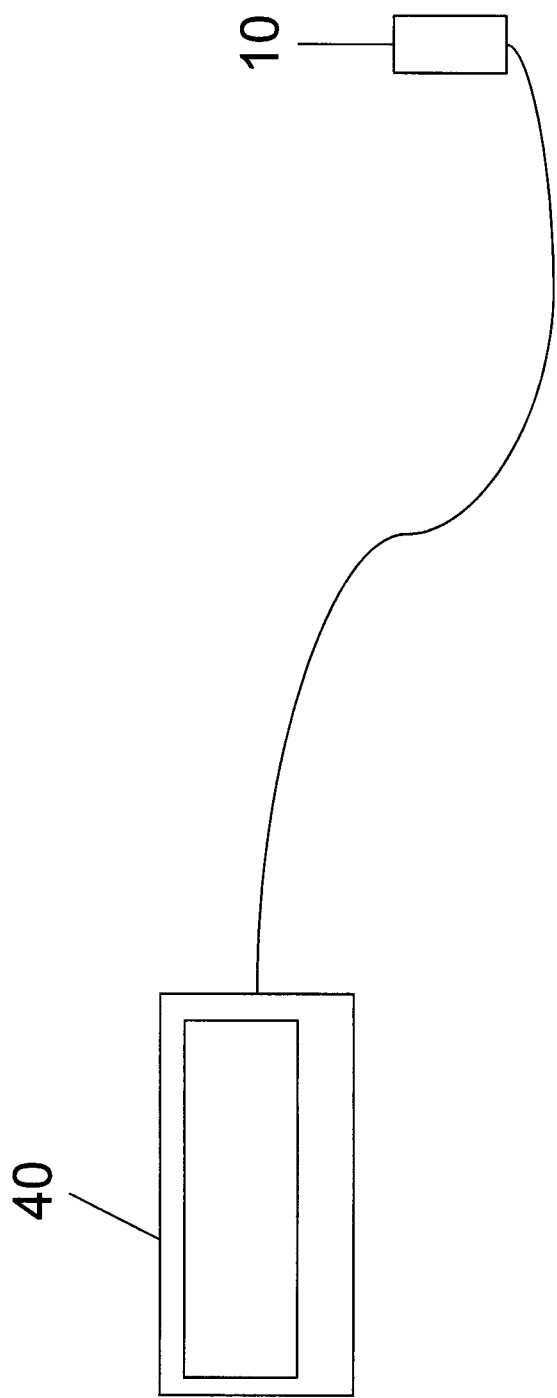
FIG. 3 illustrates a system incorporating the device of FIG. 1.

A device 10 for measuring a parameter of cardiac function in a patient as previously described in WO 2008/098353 is shown in FIG. 1A. The device 10 comprises a light source 20 that emits light in the 400 nm to 1000 nm wavelength range, e.g. visible and infra-red light, a photodetector 30 adapted to receive light from the light source 20 (as shown in FIG. 2) and translate the received light into an output signal and a patch probe 28 for placement on a patient at an external site in the vicinity of a cardiac blood vessel (as shown in FIG. 1B) which functions as the interface of the device between light source 20/photodetector 30 and a selected external patient site. Thus, the probe 28 permits/facilitates delivery of light emitted by the light source 20 to the selected patient site and transfer of light reflected from or transmitted through the patient site to the photodetector 30. To generate a visual signal, the device 10 may additionally comprise a signal-processing component 40 (FIG. 3) which communicates with the photodetector 30 to translate light received by the photodetector 30 into a recordable visual signal or waveform of the cardiac vessel (e.g. representative of a time course plot of a measurable characteristic or parameter of the blood vessel such as a pressure waveform or central venous pulse).

The light source 20 may be any suitable light source such as a laser diode (e.g. RLT7605G, 760 nm, 5 mW, sm, 9.0 mmh, or RLT8510MG, 850 nm, 10 mW, sm, 5.6 mm), a light emitting diode (LED) or a broadband light source emitting a selected wavelength in the range of 400 nm to 1000 nm, for example, a wavelength in the range of 780 nm and 850 nm. In an embodiment, the light source is adapted to emit light in two or more wavelengths, e.g. by association with a frequency oscillator. The light source 20 is powered by an appropriate power supply 18 such as a 12V DC power supply. Light from the light source 20 is directed to at least one external tissue site on the patient that is within close proximity to a cardiac blood vessel, such as the internal jugular vein, the external jugular vein and the carotid artery, while the internal jugular vein is preferred. The neck, for example, represents a suitable site for monitoring a cardiac parameter.

As shown in FIG. 5A/5B, in one embodiment, light from the light source 20 may be directed or focussed by an optical lens 22 into a transmitting means 24, such as transmitting optical fibre bundles, for transmission to the selected patient site. Receiving means 26, such as optical fibre bundles, may also be used to receive light that is reflected/transmitted from the patient site and convey this light to photodetector 30 (FIG. 5A). As one of skill in the art will appreciate, each fibre optic bundle will incorporate fibres manufactured of material appropriate for the transmission of the wavelength of the light emitted from the light source 20. For example, if the light source 20 emits in the visible wavelength range, both multiple mode plastic and glass optical fibres may be used. The number and diameter of the fibres in the fibre optic bundle is optimized empirically to provide the highest signal to noise ratio in a given application. In the embodiments shown in FIG. 5A/5B, the transmitting and receiving optical fibre bundles 24, 26 are set in the patch probe 28, either at distinct spaced sites or they may be combined together at a single site.

As shown in FIG. 6A/6C, optical mirrors 29 may be utilized to direct or reflect light from the transmitting fibre bundle 24 into the tissue at the selected patient site, and to direct reflected or transmitted light from the patient site into the receiving fibre bundle 26 (FIG. 6A). Alternatively, the light source 20 and photodetector 30 may be set directly in the patch probe 28 obviating the need for optical fibres as shown in FIG. 6B. In yet another embodiment, a combination of the foregoing embodiments may be utilized in which the light source 20 is set directly in the probe 28 to deliver light to the patient site, while the reflected/transmitted light is received by optical fibres 26 for delivery to the photodetector 30. A converse embodiment may also be used in which the probe 28 comprises transmitting optical fibres 24 to deliver light from the light source to the patient site, and a photodetector 30 set directly in the probe 28 to receive the reflected/transmitted light (FIG. 6C). Accordingly, the light source 20 and photodetector 30 are each coupled to the probe 28 (e.g. attached to, integrally formed with or set directly in the probe 28).

The light source 20 or transmitting optical fibres 24 may be set in the same patch probe 28 as the photodetector 30 or receiving optical fibres 26, or in a separate patch probe 28 for placement at a distinct site on the patient that is within a suitable distance from the photodetector 30 or receiving optical fibres 26 to permit detection of reflected/transmitted light. The distance between the component delivering light to the patient site (light source or transmitting optical fibres) and the component receiving light from the patient site (photodetector or receiving optical fibres) may vary depending on the nature of each of the components, while a typical distance is generally between 2 and 4 cm, for example, 3 cm.

The patch probe 28 may be made out of any material suitable to support the electronic/optical components it houses, e.g. light source, photodetector, optical fibres or mirrors, and which is compatible for placement on the skin. An example of one such suitable material is medical rubber. The patch 28 may be held in position manually, may be held in position by adhesives (one side of the patch may be coated with a material that is adhesive to skin such as a hydro gel adhesive) or may be adapted to be held in place with straps that can be tied or otherwise secured. Opposing ends of the band may also include an adhesive material such as Velcro to facilitate their attachment and to hold the device in place.

The photodetector 30 translates received reflected/transmitted light into a recordable output such as current or voltage. An example of a suitable photodetector 30 for use in the present device is a silicon photo diode (e.g. Hamamatsu S8553). Condensor lenses may be incorporated, if required, to refocus the reflected or transmitted beam of light to be received by the photodetector 30. As will be understood by a person skilled in the art, silicon photodiodes are semiconductor light sensors that generate a current or voltage when the P-N junction in the semiconductor is illuminated by light. Accordingly, the photodetector 30 provides a current/voltage signal in response to the received light signal. Thus, the current/voltage signal output generated by the photodetector 30 is proportional to the instantaneous light intensity of the light signal received at the photodetector 30. Accordingly, the photodetector 30 provides a time-varying output (e.g. current/voltage as a function of time) which is dependent upon the received light and its characteristics.

Figure 5:
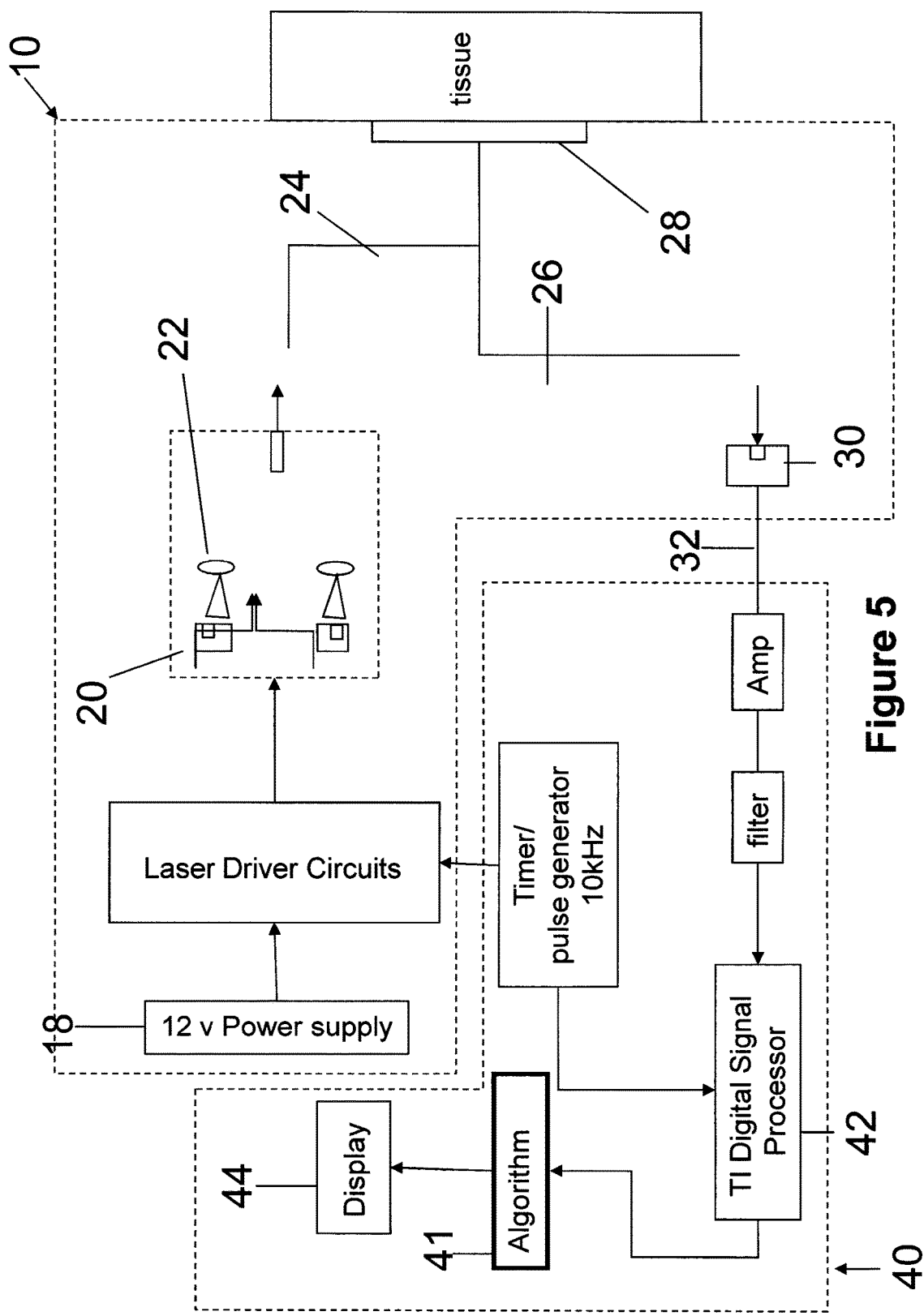
FIG. 5 is a block diagram of a system incorporating a device as in FIG. 1.
Figure 8:
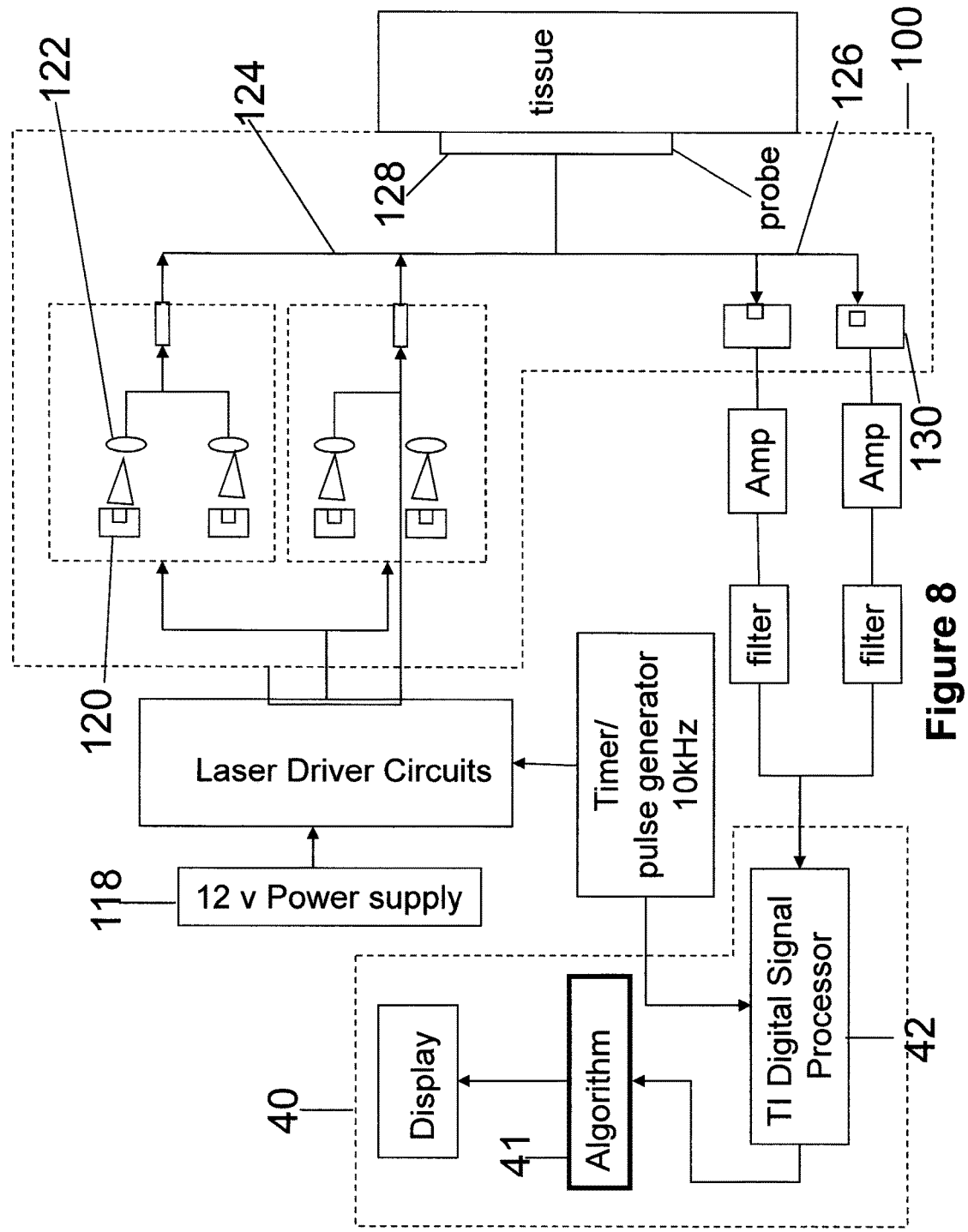
FIG. 8 is a block diagram of a system incorporating a device as in FIG. 7.
Figure 16:
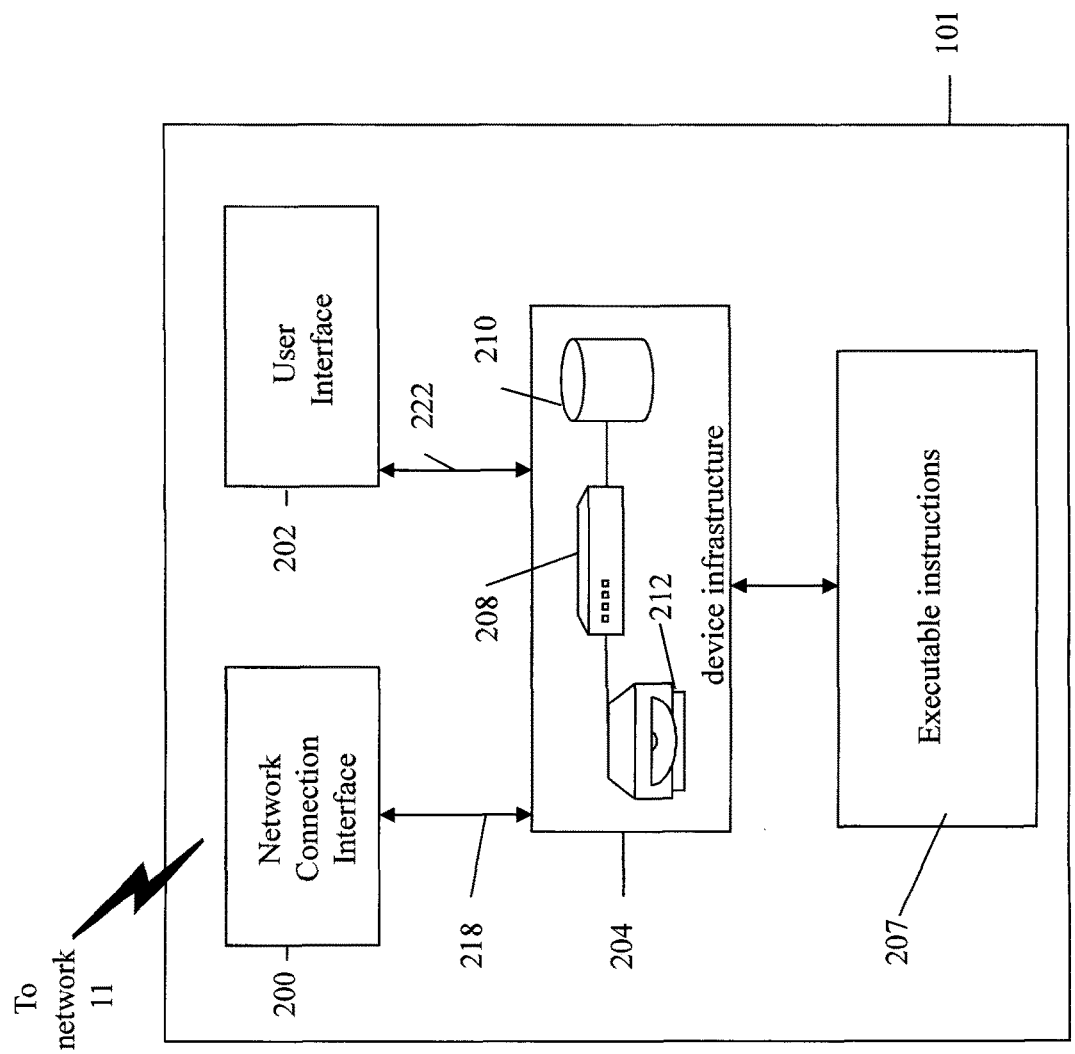
FIG. 16 is a block diagram illustrating a system according to an aspect of the invention.

In an aspect of the invention, a system is provided, for example as shown in FIG. 5, 8 or 16, in which the photodetector 30 of device 10 is connected to a signal processing device 40. The signal processing device 40 is operable to receive the signal provided by the photodetector 30 (e.g. the time varying current/voltage signal) and translate the signal into a visual output such as a waveform. Thus, the signal processing device 40 is operable to digitize the output provided by the photodetector 30 into a recordable output for presenting on a display (e.g. 44).

Referring to FIG. 5 or 8, a system is provided comprising at least one light source 20 for emitting light, a probe 28 for facilitating the delivery of light to an external tissue site on the patient, at least one photodetector 30 configured for receiving light emitted by the light source 20 (which is either reflected from or transmitted through the tissue site) and translating the light to a current/voltage signal in response thereto, a signal processing device 40 for translating the signal from the photodetector 30 into a visual output such as a time-varying waveform. As will be described below, the signal processing device 40 may include a microprocessor (e.g. digital signal processor, Texas Instruments) or digital acquisition board 42 to digitize the signal (e.g. current/voltage) from the photodetector 30, and a display unit 44, such as a monitor, which is in communication with or connected to the microprocessor 42 (FIG. 5), and functions to display the signal as a waveform.

Alternatively, as will be understood by a person of skill in the art and as shown in FIG. 5B, the signal processing device 40 may be separate from the display unit 44, and in communication with an external display unit 44 for presenting the output of the signal processing device 40 thereon. For convenience, the display unit, e.g. monitor, may be portable, e.g. a handheld unit, and/or battery operated. Such a handheld unit may be connected by a cable to a patch probe 28 including the light source(s) and photodetector(s). The system may further include a docking station for docking and charging a handheld monitor, or a docking station for the probe 28, optionally including a unit adapted to calibrate the probe.

According to another embodiment, the signal processing device 40 may further comprise an algorithm processing module 41 (e.g. illustrated in FIG. 8) for receiving an indication of the desired cardiac parameter output (e.g. via a user interface or predefined selection of the desired cardiac parameter). The algorithm processing module 41 is operable to translate the signal received from the photodetector 30 into the desired cardiac parameter output (e.g. blood pressure waveform).

Referring to FIG. 16, the signal processing device 40 can be implemented on one or more respective computing device(s) 101. The devices 101 in general can include a network connection interface 200, such as a network interface card or a modem, coupled via connection 218 to a device infrastructure 204. The connection interface 200 is connectable during operation of the device(s) 101 to a network 11 (e.g. an intranet and/or an extranet such as the Internet) which enables the device(s) 101 to communicate with each other as appropriate. The network 11 can, for example, support the communication of the output signal (e.g. current/voltage signal) provided by the photodetector 30 to the signal processing device 40.

The device(s) 101 may also have a user interface 202, as also shown in FIG. 16, coupled to the device infrastructure 204 by connection 222 to interact with a user. The user interface 202 can include one or more user input devices such as, but not limited to, a QWERTY keyboard, a keypad, a trackwheel, a stylus, a mouse, a microphone and a user output device such as an LCD screen display and/or a speaker. If the screen is touch sensitive, then the display can also be used as the user input device as controlled by the device infrastructure 204.

Operation of the device(s) 101 is facilitated by the device infrastructure 204. The device infrastructure 204 includes one or more computer processors 208 (e.g. a Digital Signal Processor) and can include an associated memory 210 (e.g. a random access memory). The computer processor 208 facilitates performance of the computing device 101 configured for the intended task through operation of the network interface 200, the user interface 202 and other application programs/hardware 207 of the computing device 101 by executing task-related instructions. These task-related instructions may be provided by an operating system and/or software applications 207 located in the memory 210, and/or by operability that is configured into the electronic/digital circuitry of the processor(s) 208 designed to perform the specific task(s). Further, it is recognized that the device infrastructure 204 may include a computer readable storage medium 212 coupled to the processor 208 for providing instructions to the processor 208. The computer readable medium 212 can include hardware and/or software such as, by way of example only, magnetic disks, magnetic tape, optically readable medium such as CD/DVD ROMS, and memory cards. In each case, the computer readable medium 212 may take the form of a small disk, floppy diskette, cassette, hard disk drive, solid-state memory card or RAM provided in the memory module 210. It should be noted that the above listed examples of computer readable media 212 may be used either alone or in combination. The device memory 210 and/or computer readable medium 212 may be used to store, for example, the desired output (e.g. pressure waveform) for use in processing of the signal received from the photodetector 30.

Further, it is recognized that the computing device(s) 101 may include executable applications 207 comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example. Accordingly, the functionality of the signal processing device 40 and/or the photodetector 30 may be implemented in hardware, software or a combination of both. Accordingly, the use of a processor 208 as a device and/or as a set of machine-readable instructions is hereafter referred to generically as a processor/module for the sake of simplicity.

It will be understood that the computing device(s) 101 may be, for example, personal computers, personal digital assistants, mobile phones, and content players. Further, it is recognised that each server computing device 101, although depicted as a single computer system, may be implemented as a network of computer processors, as desired.

Referring to FIG. 8, the signal processing device 40 may execute an algorithm (e.g. via the algorithm processing module 41) to translate the signal received by the photodetector 30 to a waveform. The waveform is the time varying component of the optical signal associated with cardiac activities, which can be translated into dynamic information such as blood flow, flow velocity, blood volume, blood pressure and blood content such as oxygenation or physical displacement of blood within the vessel.

In one embodiment, for example, the signal is translated into a pressure waveform. Since the central venous pressure waveform is proportional to the blood volume inside the jugular vein, and the amplitude of the received signal from the photodetector (e.g. the current/voltage signal) is inversely proportional to the blood volume, the central venous pressure waveform is constructed by an algorithm that inverts the signal received by the photodetector as follows:

$$P(t) \sim 1/S(t)$$

where P is the pressure waveform and S is the signal from photodetector (e.g. the current/voltage signal).

The absorbance values collected at regular user-determined intervals, for example, 10 data points/mm, are stored as a spreadsheet associated with a cardiac parameter or cardiac output. The display unit 44 functions in real-time to display the selected blood vessel waveform according to an executed algorithm (via the algorithm processing module 41) against time which can be used as described below to calculate, for example, a cardiac parameter or cardiac output.

Figure 4:
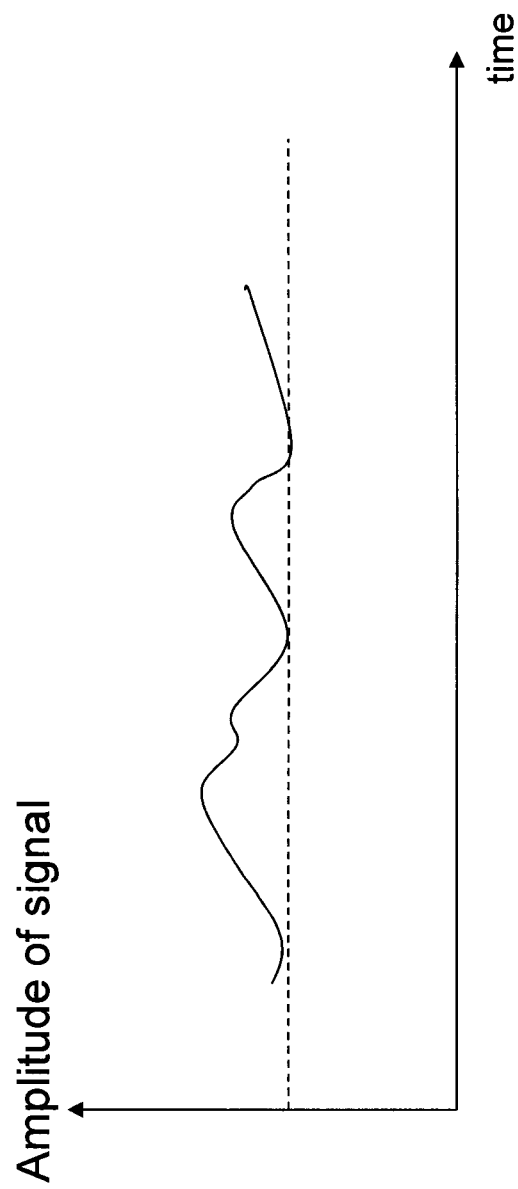
FIG. 4 illustrates a signal or waveform produced using a device as in FIG. 1.

A sample display of a waveform (e.g. generated based on a signal obtained by the photodetector and processed by a signal processing device 40) obtained using the present device is shown in FIG. 4. As can be seen, there is a time course variation in the signal detected by the photodetector 30 that results from a selected blood vessel pulse, changes in the blood volume and content (such as oxygen saturation) inside the blood vessel. The blood volume and content in the selected blood vessel affects the absorption of light, thereby resulting in a signal with varying amplitude. For example, as the jugular vein pulse increases and decreases the blood volume in the jugular vein, the amplitude of the detected optical signal (e.g. as received by photodetector 30) will decrease and increase, respectively. The time course plot of the amplitude of the recorded signal reflects the waveform of the jugular vein pulse.

In another embodiment of the present invention, a device 100, operable to measure blood content, such as the blood oxygen saturation of central venous blood, is provided. As the jugular vein, especially the right internal jugular vein, is directly connected to the superior vena cava as shown in FIG. 1, the jugular vein waveform is representative of the parameters of central venous blood.

Figure 7:
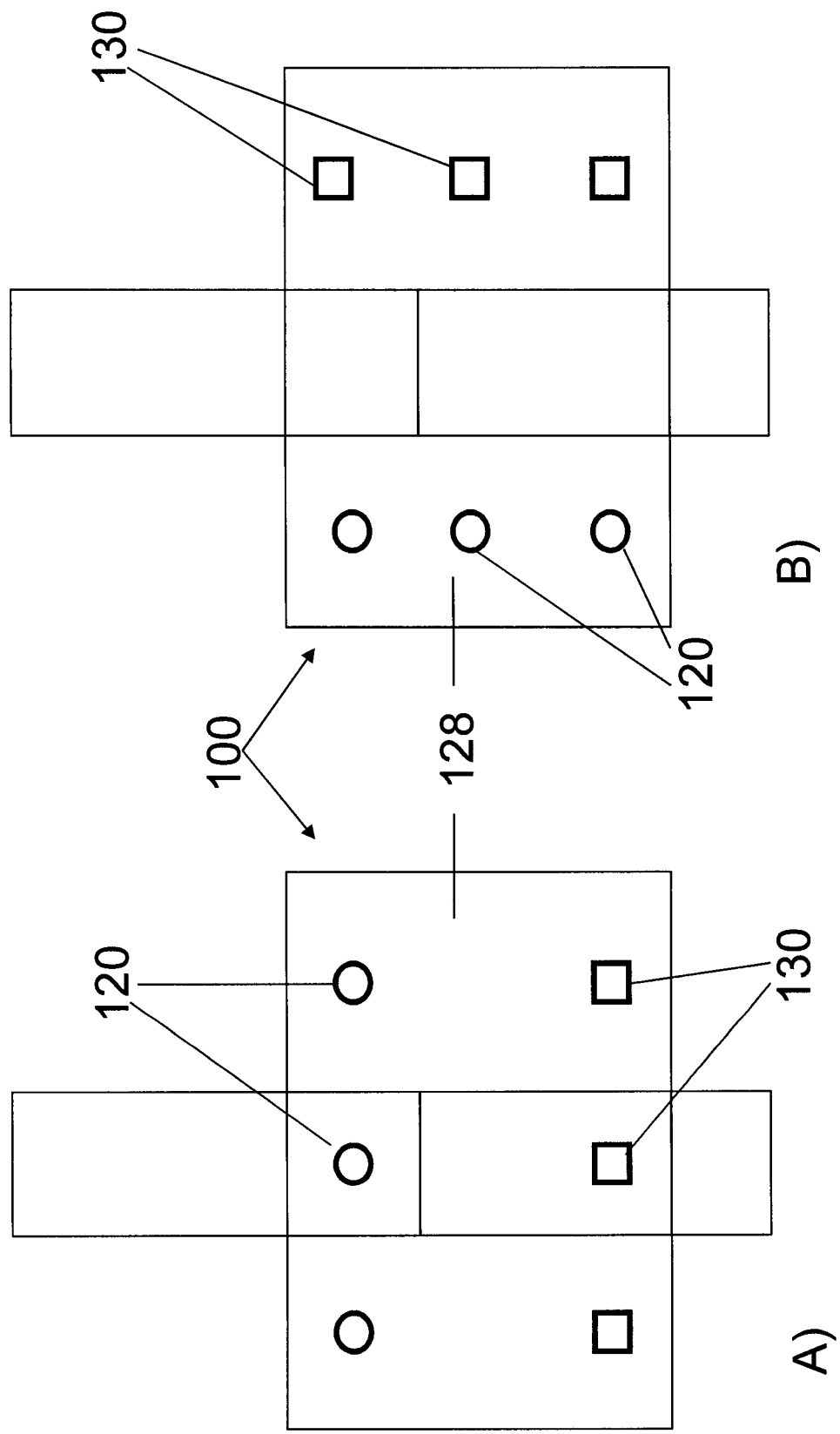
FIG. 7 illustrates a top view of embodiments of the invention (A, B) comprising multiple light sources and photodetectors.

For this utility, the device 100, as shown in FIGS. 7 and 8, comprises at least two light sources 120, each emitting light of a different wavelength within the range of 400 nm to 1000 nm. The device also comprises a photodetector 130 for each light source 120 adapted to receive the transmitted or reflected light at a given wavelength. As set out above, each light transmitting component (e.g. light source 120 or transmitting optical fibres 124) and light receiving component (e.g. photodetector 130 or receiving optical fibres 126) is set in a patch probe 128, and may be arranged as shown in FIG. 7A or 7B; however, as one of skill in the art will appreciate, alternative arrangements of the light-transmitting components and light-receiving components exist which will not affect the function of the device 100. For example, the device 100 may comprise multiple patches probes 128, each of which includes a light-transmitting component and a light-receiving component. Alternatively, the device 100 may comprise a single patch 128 including multiple light-transmitting components and light-receiving components. In another alternative, the device 100 may comprise a first patch 128 with one or more light-transmitting components and light-receiving components, and a second patch with one or more light-transmitting components and corresponding light-receiving components. As set out above, regardless of the number of patches and arrangements thereof, the device may be incorporated within a system as described above comprising a signal receiving device 140 and to translate the output of the photodetector 130 into, for example, a desirable form.

The time course variation in the detected signal associated with a cardiac vessel pulse at different wavelengths may be used to calculate the blood content, such as blood oxygen saturation, and other parameters associated with the cardiac vessel pulse. There are various ways to calculate blood oxygen saturation as a function of variations in the detected signal caused by cardiac vessel pulse at multiple light wavelengths, e.g. at 780 nm and 850 nm. As one of skill in the art will appreciate, the selected wavelengths for use in blood content determination will vary with the blood parameter being determined. For example, wavelengths of 690 nm and 830 nm, may be used to obtain deoxygenated haemoglobin and oxygenated haemoglobin content, respectively. A wavelength of 950 nm may be used to obtain water content of blood. Moreover, the blood parameter of interest may be determined through photon diffusion equations, photon transportation equations or Modified Beer Lambert's Law as will be described.

Modified Beer Lambert's Law

The detected signal (e.g. current) may be expressed as:

$$I_{\lambda_1} = I_{0,\lambda_1} e^{-B[\varepsilon_{Hb,\lambda_1} \cdot (C_{Hb} + \Delta C_{Hb}) + \varepsilon_{HbO,\lambda_1} \cdot (C_{HbO} + \Delta C_{HbO})]L + A} \quad (1)$$

where:

$I_{\lambda_1}$ is the signal provided by the photodetector at wavelength $\lambda_1$, $I_{0,\lambda_1}$ is the signal from the light source at wavelength, $\lambda_1$, $C_{Hb}$, $C_{HbO}$ are the concentrations of deoxygenated and oxygenated hemoglobin of steady tissue medium blood;

$\Delta C_{Hb}$, $\Delta C_{HbO}$ are the changes in the concentrations of deoxygenated and oxygenated hemoglobin caused by the jugular vein pulse;

$\varepsilon_{Hb,\lambda_1}$, $\varepsilon_{HbO,\lambda_1}$ are the absorption properties of deoxygenated and oxygenated hemoglobin at wavelength $\lambda_1$ for the purposes of calculating blood oxygen saturation; and A B are constants determined by boundary conditions.

The relative change in signal from the signal emitted from the light source to the signal detected by the photodetector which is caused by the jugular vein pulse is represented for a first wavelength by:

$$\Delta I_{\lambda_1} = e^{-B[\varepsilon_{Hb,\lambda_1} \cdot (\Delta C_{Hb}) + \varepsilon_{HbO,\lambda_1} \cdot (\Delta C_{HbO})]L} \quad (2)$$

or as $$OD_{\lambda_1} = \ln(\Delta I_{\lambda_1}) = -B(\varepsilon_{Hb,\lambda_1} \cdot \Delta C_{Hb} + \varepsilon_{HbO,\lambda_1} \cdot \Delta C_{HbO}). \quad (3)$$

Similarly, the change in signal between emitted and detected signal for a second light wavelength is represented by:

$$OD_{\lambda_2} = \ln(\Delta I_{\lambda_2}) = -B(\varepsilon_{Hb,\lambda_2} \cdot \Delta C_{Hb} + \varepsilon_{HbO,\lambda_2} \cdot \Delta C_{HbO}) \quad (4).$$

Blood oxygenation derived from jugular vein pulse is then determined using the following equation:

$$S_{jv}O_2 = \frac{\Delta C_{HbO}}{\Delta C_{Hb} + \Delta C_{HbO}} \quad (5)$$

$$= \frac{\varepsilon_{Hb,\lambda_1} \cdot OD_{\lambda_2} - \varepsilon_{Hb,\lambda_2} \cdot OD_{\lambda_1}}{(\varepsilon_{Hb,\lambda_1} - \varepsilon_{HbO,\lambda_1}) \cdot OD_{\lambda_2} - (\varepsilon_{Hb,\lambda_2} - \varepsilon_{HbO,\lambda_2}) \cdot OD_{\lambda_1}}$$

In use, the patch probe 28 of device 10 comprising light source(s) 20 and photodetector(s) 30 is generally placed on the neck of the patient at a site near a selected blood vessel, for example, the internal jugular vein. It is desirable for the patient to be lying down at about a 30 degree incline from the horizontal. The patient maintains regular breathing during the process of measuring the pulse of the blood vessel, e.g. blood volume in the blood vessel. Light from the light source 20 is either reflected off of, or transmitted through, the target site on the patient's neck, and detected by the photodetector 30. The photodetector 30 translates the detected light into an output signal (e.g. current/voltage) that may be digitized for expression as amplitude as a function of time to result in a waveform of the selected blood vessel pulse. The amplitude of signals obtained using different wavelengths may be used according to Lambert's law as above to determine blood oxygenation.

Since organ tissue, such as neck tissue, is generally heterogeneous, as a result, it exhibits different attenuation effects to near infrared light. Thus, different sites on a patient's neck, or the neck tissue of different patients, may result in undesirable variances in the amplitude of pulse signals to yield inaccurate determination of, for example, venous blood oxygenation. This means that the attenuation effects of the surrounding tissue to the jugular vein cannot be viewed as constant and thus the calculation of venous blood oxygenation must be corrected to accommodate these attenuation variances.

Figure 19:
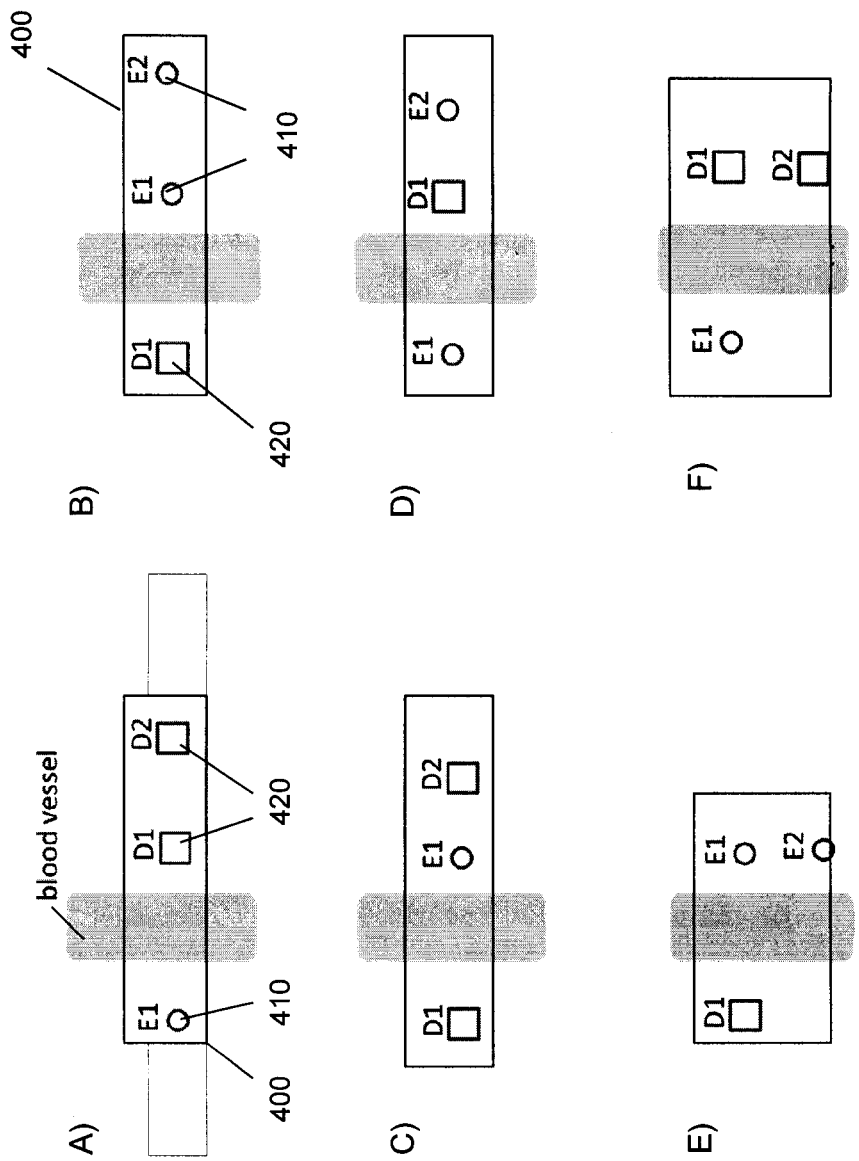
FIG. 19 illustrates attenuation correction devices (A-I) in accordance with another aspect of the invention.

An attenuation correction device 400 for use to determine venous blood oxygenation that is corrected for such attenuation differences is also provided herein as illustrated in FIG. 19. The device 400 comprises at least one light source (E1) 410 that is capable of emitting light of two different wavelengths in the 400 nm to 1000 nm wavelength range. Examples of suitable wavelength pairs to be used include, but are not limited to, (w1 is 660 nm and w2 is 880 nm), (w1 is 660 nm and w2 is 905 nm) and (w1 is 660 nm and w2 is 940 nm). The device 400 also comprises at least one photodetector (D1) 420 capable of detecting two different wavelengths of light emitted by the light source(s). Thus, the device may comprise one light source and two photodetectors (FIG. 19A/C/F), two light sources and one photodetector (FIG. 19B/D/E), or two light sources and two photodetectors (Fig. G/H/I). The distance between each light source and photodetector must be different (by at least about 1 mm), the distance between light source and photodetector ranging between about 0.5 cm to about 10 cm. The device 400 also includes a patch probe, similar to patch probe 28 described above, which permits/facilitates delivery of light emitted by the light source(s) to the selected patient site and transfer of light reflected from or transmitted through the patient site to the photodetector(s).

Using a device as shown in FIG. 19A, for example, light of a first wavelength is emitted from a light source or light emitter 1 (E1) and detected by a photodetector 1 (D1) is recorded as: $I_{E1D1}$, continuously, and light of a second wavelength is emitted from E1 and detected by photodetector 2 (D2) is recorded as: $I_{E1D2}$, continuously. The distance between E1 and D1 is different from the distance of E1 and D2. Each recorded optical signal has an AC part which is caused by blood pulse and DC part which is caused by the overall tissue media including the blood vessels. The optical attenuation (OD) at a given wavelength, w, is obtained by comparing the average light intensities (DC) measured through different light source (or emitter) and detector pairs over time (reflects the property of steady tissue media–DC is constant when there is no pulse). The optical attenuation at wavelength, w, can be calculated as:

$$OD_w = \ln\left(\frac{DC_{E1D1}}{DC_{E1E2}}\right)$$

or $$OD_w = \frac{DC_{E1D1}}{DC_{E1E2}}$$

The attenuation correction factor (C) of optical attenuation difference between two wavelengths, w1 and w2, is obtained by comparing the OD at the two different wavelengths:

$$C = \frac{OD_{W1}}{OD_{W2}}$$

and this correction factor can be used to correct venous blood oxygenation determination. C is variable when tissue oxygenation or when venous blood oxygenation changes.

In one embodiment, the attenuation correction device 400, can itself be used to determine venous blood oxygenation based on the standard oximeter equation as follows:

$$S_{jv}O_2(\text{non corrected}) = A + B*R$$

where $R = (AC/DC)_{w1}/(AC/DC)_{w2}$; and
A and B are constants which are determined through standard pulse oximeter calibration procedures (as is well-established in the art), incorporating the attenuation correction factor, C, as follows:

$$S_{jv}O_2(\text{corrected}) = A + B*(C*R)$$

Figure 6:
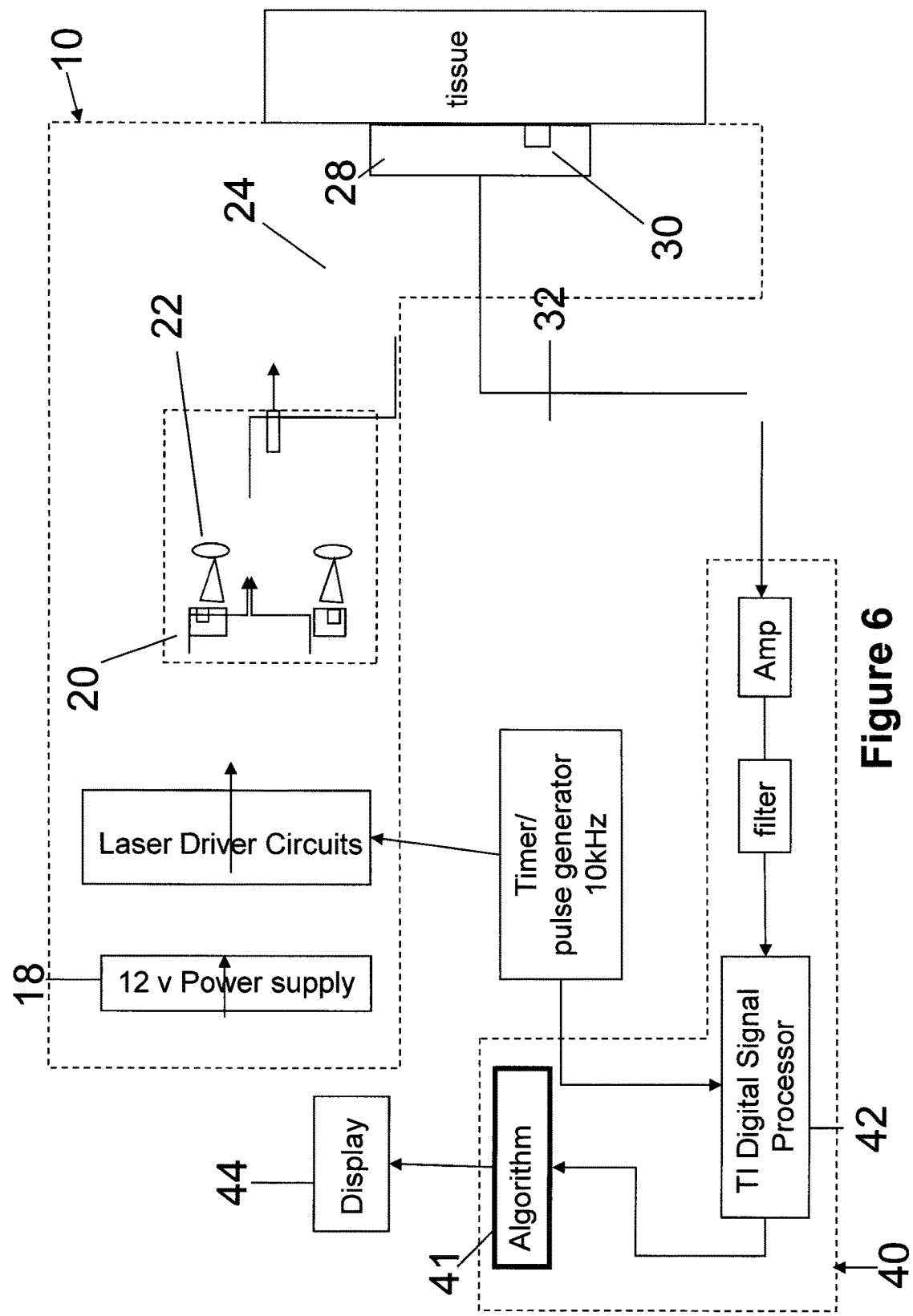
FIG. 6 is a block diagram of another system incorporating a device as in FIG. 1.
Figure 13:
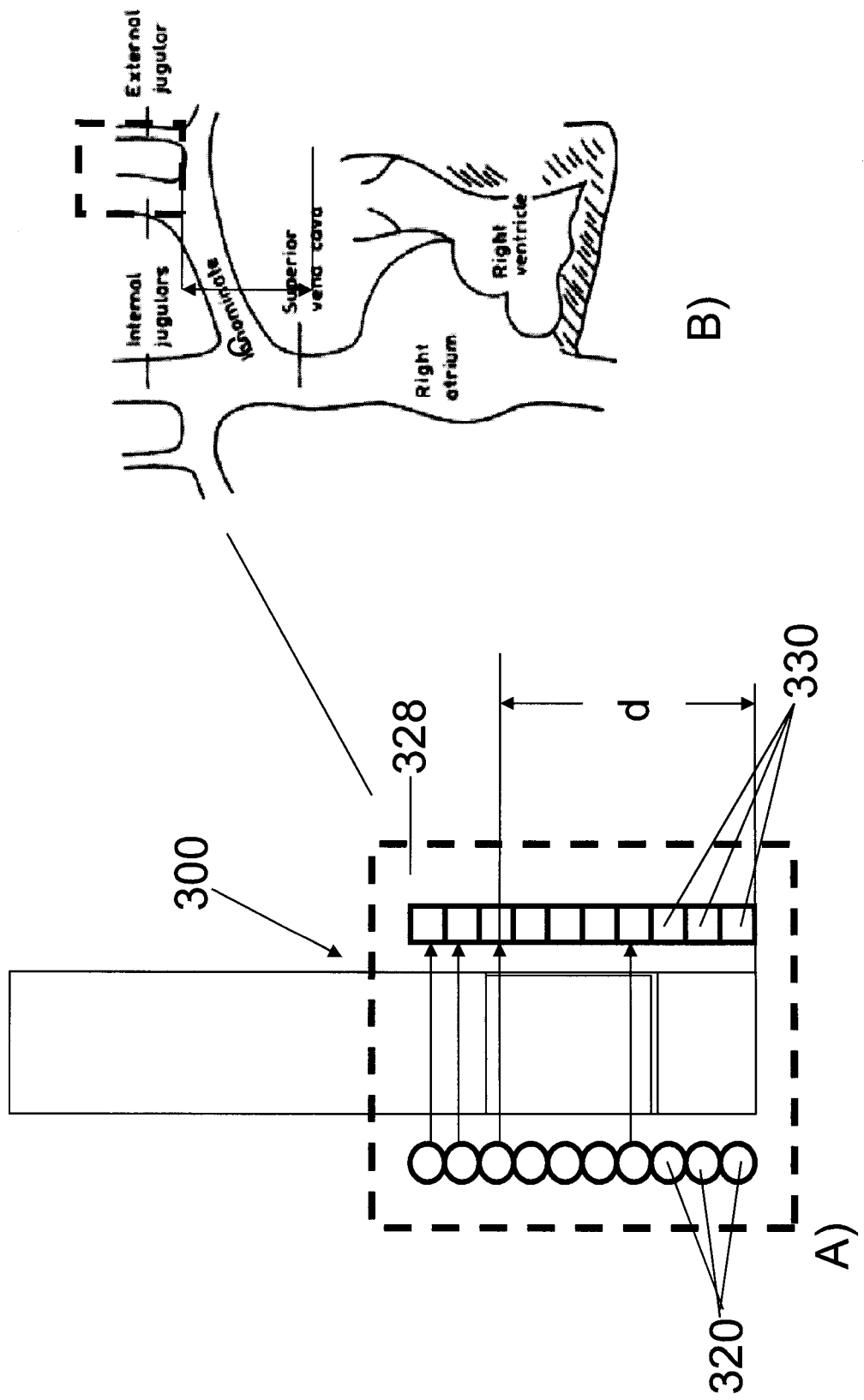
FIG. 13 illustrates a top view of a device in accordance with a further aspect of the invention (A) and a view of its placement on the neck of a patient (B)
Figure 14:
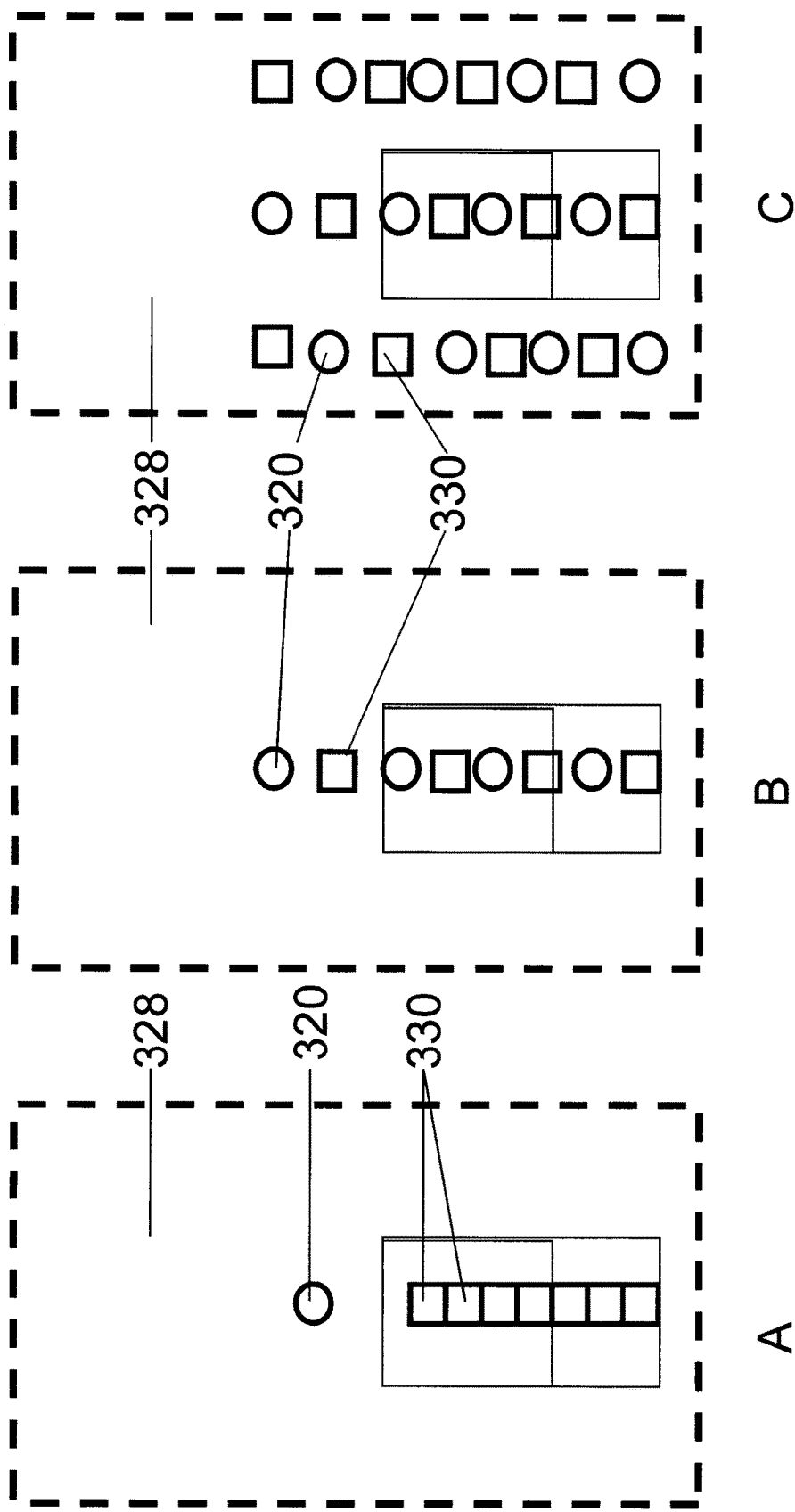
FIG. 14 illustrates different source-detector configurations (A, B and C) of a device useful to measure blood pressure.

Alternatively, the attenuation correction device 400 may be utilized in a system comprising an optical device 10 to determine venous oxygenation which is connected to a signal processing device 40, and a device 400 to determine attenuation correction which is also connected to the signal processing device 40. The signal processing device 40 is operable to receive the signal provided by the photodetector(s) of optical device 10 and the photodetector(s) of device 400, translate the signals therefrom, and execute an algorithm that calculates measured venous oxygenation, attenuation correction and corrected venous oxygenation. Examples of optical devices 10 that may be used to determine venous blood oxygenation are shown in FIG. 1A, FIG. 13 and FIG. 14. The system may be as shown in FIG. 5 or 6, additionally incorporating an attenuation correction device 400 in communication with the signal processing device 40.

In addition to the foregoing, the attenuation correction device 400 may be used in conjunction with other devices for use to determine venous blood oxygenation, such as conventional pulse oximeters.

Figure 9:
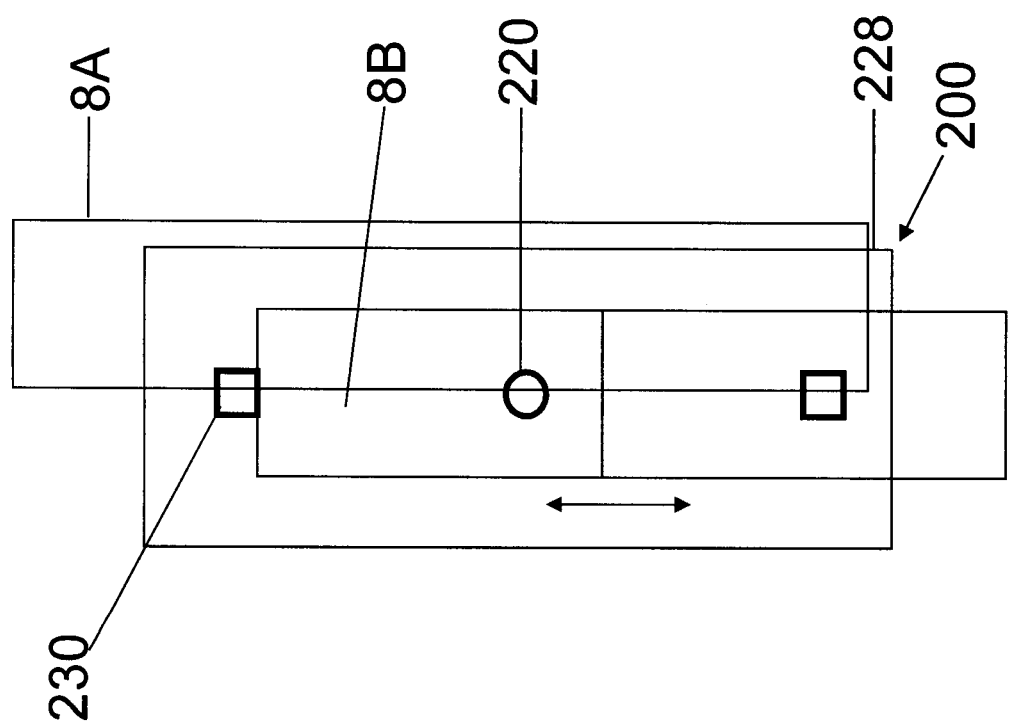
FIG. 9 (A-C) illustrates a top view of embodiments of the invention comprising multiple photodetectors per light source.
Figure 9:
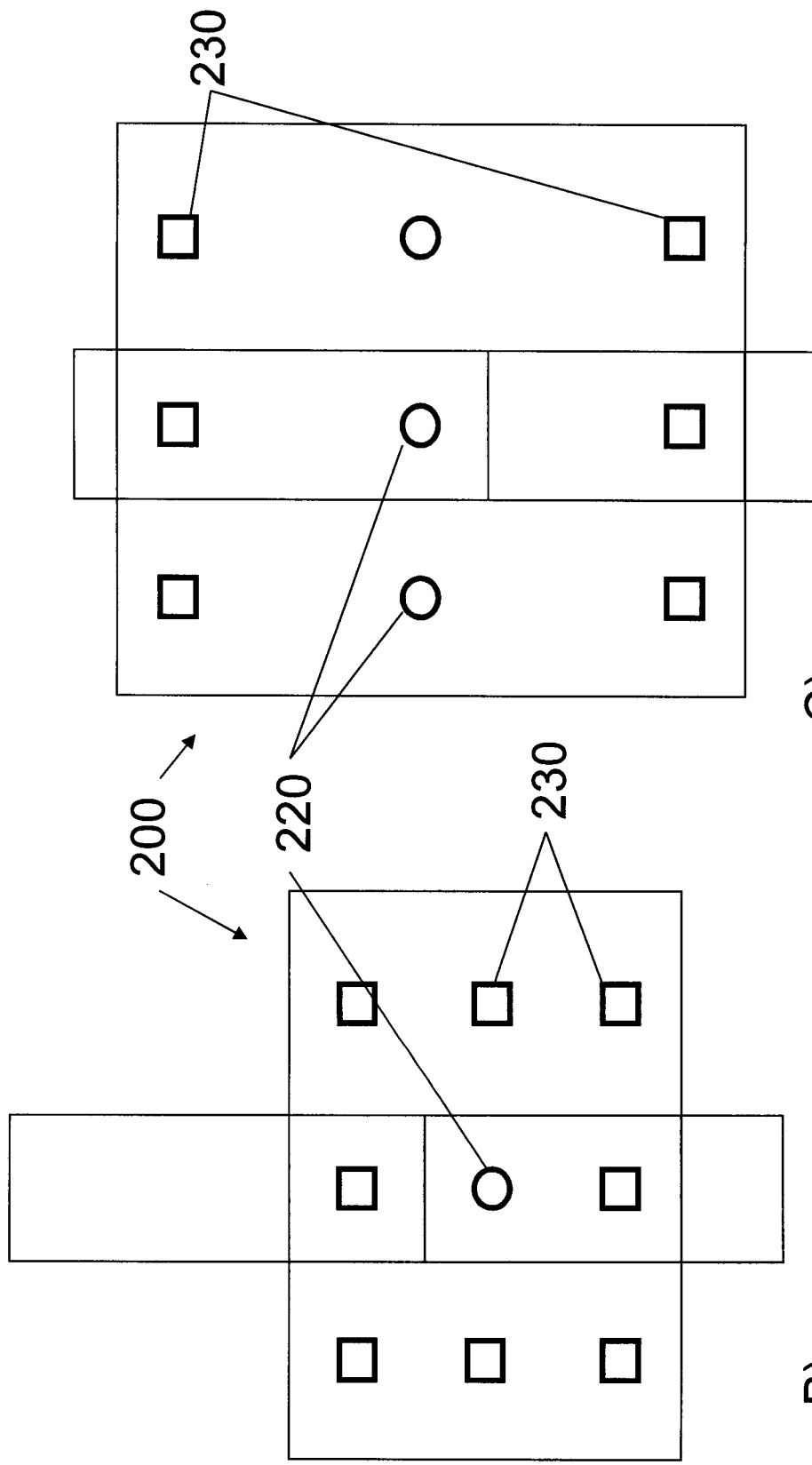

In another embodiment, illustrated in FIG. 9 (A-C), a device 200 is provided comprising one or more light sources 220, each emitting selected wavelengths of light in the 400 nm to 1000 nm range. Each light source 220 is coupled with at least two photodetectors 230 each adapted to receive light emitted at a given frequency. As discussed above, the device 200 may optionally be incorporated within a system as illustrated in FIG. 5, for example.

Figure 10:
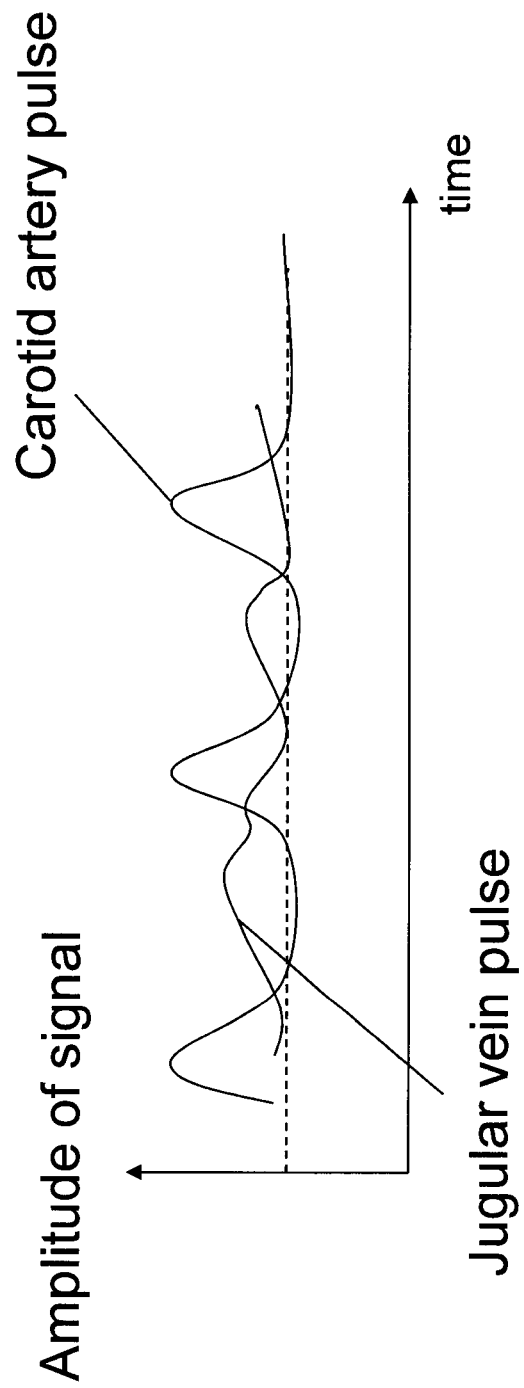
FIG. 10 illustrates a dual signal (waveform) generated by an embodiment of FIG. 9.
Figure 11:
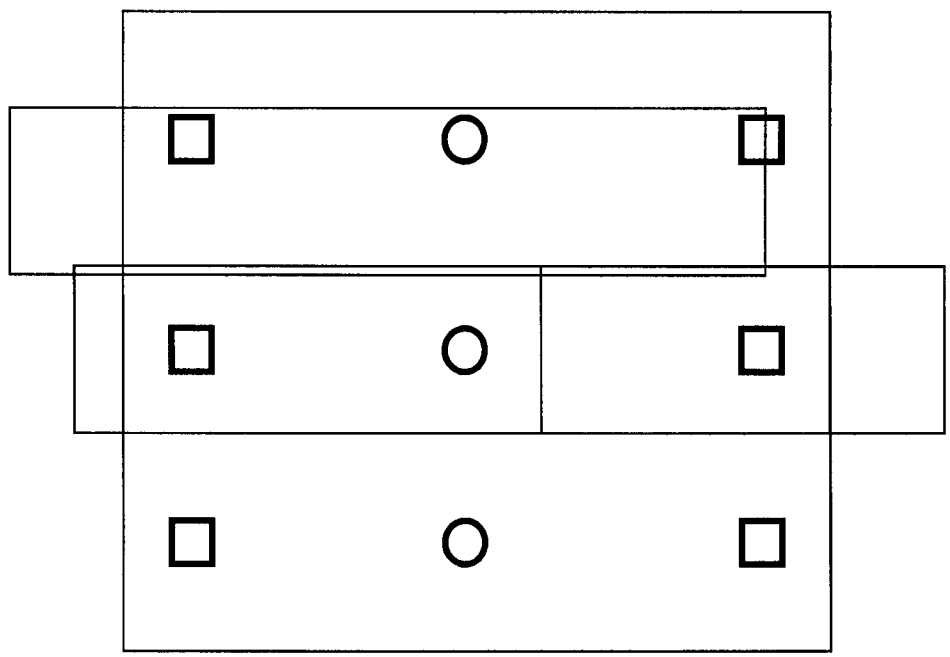
FIG. 11 illustrates a top view of a cardiac monitoring device according to an embodiment of the invention comprising multiple sensor patches.

The device 200 is useful to simultaneously measure multiple cardiac blood vessel pulses, such as jugular venous pulse as well as carotid arterial pulse, thereby generating a dual waveform as illustrated in FIG. 10, and thus, has utility to simultaneously measure arterial blood oxygenation, $S_aO_2$, in addition to central venous oxygenation, $S_{jv}O_2$, as described above. As one of skill in the art will appreciate, in the case of multiple light sources 220, each light source is turned on in sequence, and the amplitude of light emitted from the light source(s) is modulated at a selected frequency, such as 10 kHz or 20 kHz. Alternatively, light emitted by a single light source 220 can be sequentially modulated at two alternating frequencies, such as 10 kHz and 20 kHz. The output from the photodetectors (e.g. current/voltage) is filtered at a frequency selected to correlate with a given frequency emitted from a light source, for example, using a band pass filter which allows a selected frequency, such as a 10 kHz or 20 kHz signal, to pass through but blocks other frequency components in the signal.

In another embodiment, a method of measuring central venous pressure is provided. Central venous pressure is the pressure at the vena cava close to the right atrium. Abnormally high central venous pressure is an early indication of right atrial heart failure. Currently, central venous pressure is measured through invasive catheters which are inserted through the internal jugular vein to the vena cava.

A method for measuring central venous blood pressure in a patient is provided that is based on the vertical height of the jugular venous pulse, e.g. the height of the blood within a jugular vein directly reflects the central venous pressure. A determination of the highest position along the jugular vein where there is a pressure wave provides information that may be used to calculate central venous blood pressure. Thus, the method comprises the step of determining the highest position along the jugular vein to yield a waveform. The "highest position" may be measured from a known reference point, e.g. a point having a known distance from the right atrium such as the sternal angle or phlebostatic axis. The sternal angle is the angle formed by the junction of the manubrium and the body of the sternum in the form of a secondary cartilaginous joint (symphysis). This is also called the manubriosternal joint or Angle of Louis. The phlebostatic axis is located at the fourth intercostal space and ½ the anterior-posterior (AP) diameter of the chest, and approximates the location of the right atrium.

A waveform is obtained by directing a beam of light having a wavelength in the range of 400 nm to 1000 nm at an external tissue site on the patient that is in the proximity of the jugular vein, detecting light reflected from the tissue site or transmitted through the tissue site and translating the detected light into an output signal against time to generate a waveform. The highest position along the jugular vein to yield a waveform is determined when the next highest position does not yield a waveform.

Central venous pressure (P) is based on the vertical distance ($d_v$) from the right atrium to the height of the jugular venous pulse, i.e. the highest position, namely, $P = d_v$. If the reference point is the sternal angle, the mean central venous pressure may be calculated as follows:

$$P = 5 + d \cdot \sin \theta$$

wherein d is the distance from the sternal angle to the highest position that yields a waveform. The symbol, θ, is the inclined angle of the upper body of the patient relative to the horizontal position. The addition of 5 cm represents the distance from the sternal angle to the right atrium. If the reference point used is the phlebostatic axis (which approximates the position of the right atrium), central venous pressure is calculated as follows:

$$P = d \cdot \sin \theta$$

Having obtained a waveform from a cardiac vein, the central blood pressure may be calculated as follows:

$$P = a + b \frac{T}{t}$$

wherein a is a constant that relates to the position of the sensor on the neck, and b is a constant which relates to the distance between the source and the photodetector of the sensor; T is the pulse width and t is the average rise and fall time of the pulse.

In accordance with the method of measuring central venous pressure, a device 300 is provided. The device 300, as shown in FIG. 13, includes a series of light sources 320 located adjacent to one another along a length appropriate to measure the blood level in a cardiac vein, such as the internal or external jugular vein. The length will generally be about 1.5 to 10 cm. Each light source 320 emits light at a wavelength of from 600 nm to 900 nm and is associated with a corresponding photodetector 330 suitable to detect reflected or transmitted light from its corresponding light source 320. The device 300 additionally includes a patch probe 328 that functions as the interface between the light sources (320) and photodetectors (330) and is adapted for placement on a patient at a site in the vicinity of a selected cardiac blood vessel, such as a cardiac vein. The probe 328 may incorporate the light sources 320 and photodetectors 330 directly, or may instead incorporate light transmitting optical fibres and light receiving optical fibres connected to the light sources and photodetectors, respectively, or may include a combination of these, e.g. light sources and light receiving optical fibres, or light-transmitting optical fibres and photodetectors. In addition, the device 300 may be incorporated within a system as previously described including a signal-processing device to translate the output of the photodetectors into a desirable form.

In use, the device 300 is placed on the patient at an appropriate site in which a terminal light source in the series is lined up with the sternal angle. The light from each light source is detected by its corresponding photodetector. The output signal (e.g. current/voltage) of each photodetector is monitored (or transmitted to a signal processing device for translation to an alternate form of output such as a visual waveform output which is monitored) to determine whether there is an output or not. The highest position (d) along the vein to yield an output, e.g. a waveform, is then determined based on the output from each photodetector in the sequence. The mean central venous pressure (P) may then be calculated as described above.

FIG. 14 illustrates other embodiments of the device 300 that may also be useful to measure central venous pressure as described above. Each embodiment includes a different configuration of the light source(s) and photodetectors. For example, FIG. 14A illustrates a device including a single light source and an array of adjacent photodetectors that may be used to obtain an output, e.g. a waveform, sequentially along a vein to determine the highest position (d). FIG. 14B illustrates a device including sequential source-detector pairs in an alternating configuration (source-detector, source-detector, etc.) for placement along a vein as shown. FIG. 14C illustrates a device similar to that of FIG. 14B including multiple rows of alternating source-detector pairs. As one of skill in the art will appreciate, a device as shown in FIG. 1 may also be used to determine the highest position (d) along the vein to yield an output signal (e.g. a waveform) by obtaining waveform readings sequentially from the sternal angle upward along the vein. Further, as previously described, the device, regardless of its configuration may be incorporated within a system comprising a signal-processing device in order to translate the output of the photodetector into a visual output such as a pressure waveform.

Figure 17:
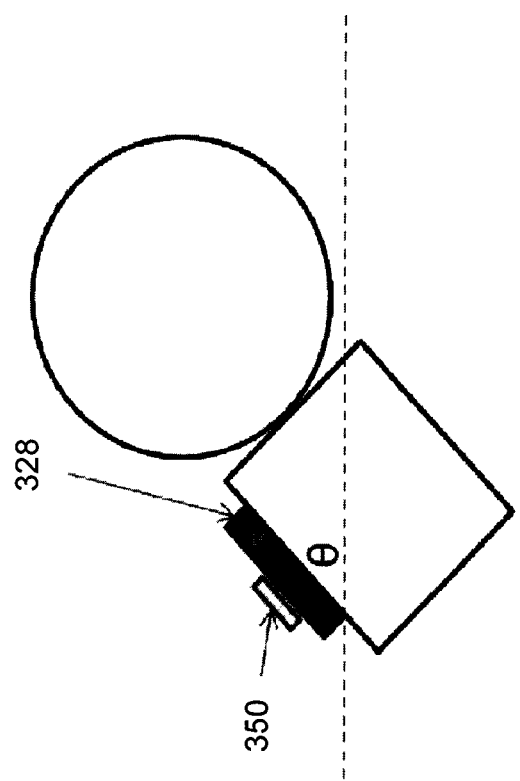
FIG. 17 illustrates the use of a pressure sensor with a device in accordance with an embodiment of the invention.

A device in accordance with the invention may additionally include an angle sensor 350 mounted on the device 328 to measure the inclined angle of the patient's upper body relative to the vertical position as shown in FIG. 17. The angle sensor may be any suitable sensor for this purpose. An example of an angle sensor is a pressure sensor, such as GE Nova Sensor NPC-100T, connected to a liquid/water tube with given length L, such as 4 cm. The pressure sensor reading P determines the vertical height H of the angle sensor according to the known formula:

$$P = \rho H$$

where $\rho$ is the density of the liquid within the tube. The inclined angle $\theta$ is thus calculated using the equation:

$$\sin\theta = \frac{H}{L}$$

Figure 18:
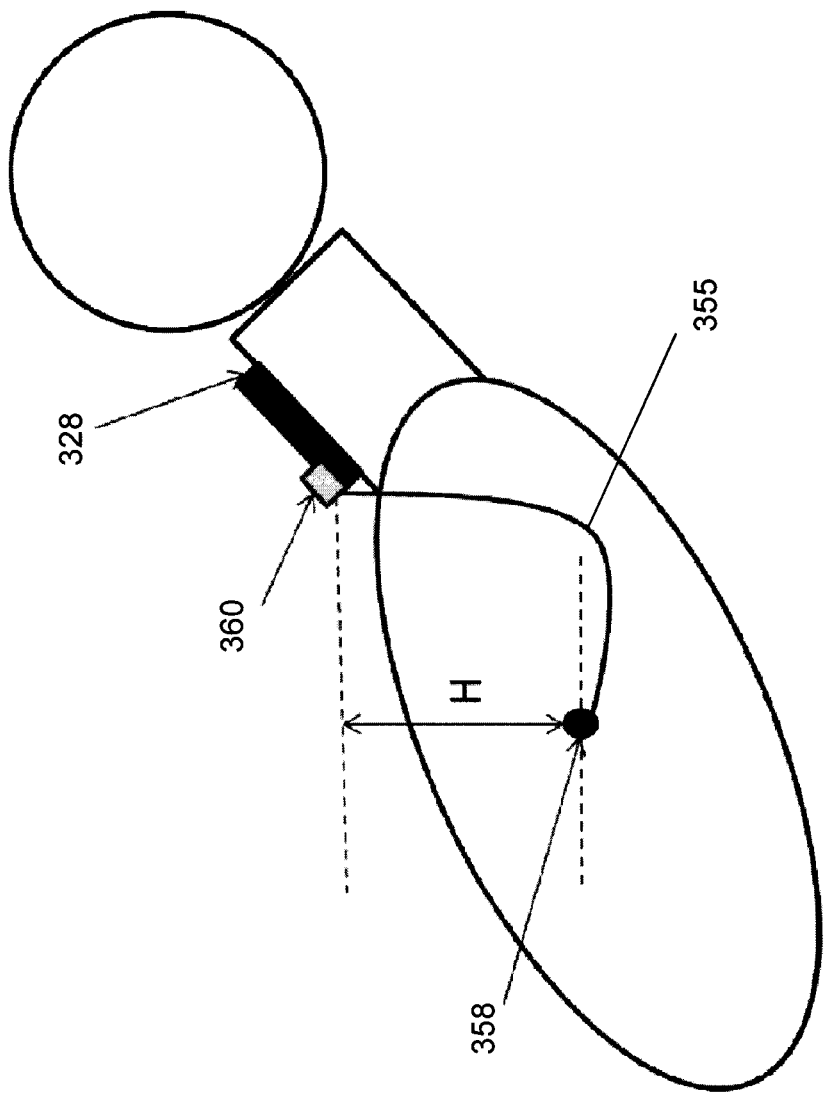
FIG. 18 illustrates the use of a height sensor with a device in accordance with an embodiment of the invention.

In another embodiment, an optical device 328 in accordance with the invention may include a height sensor 360 as shown in FIG. 18 to determine the vertical height of the "highest position" (as determined using the optical device) from the reference point. The height sensor 360 includes a reference patch 358, made of any material that is compatible for placement on the skin, e.g. medical rubber, which is placed at the reference point (e.g. sternal angle or phlebostatic axis). The reference patch 358 may be held in position manually at the reference point, may be held in position by adhesive applied to one side of the patch, e.g. a skin appropriate adhesive such as a hydrogel or may be held in place by other means, e.g. straps or Velcro, that can be tied or otherwise secured. The reference patch 358 is attached to one end of a flexible tube 355 filled with liquid such as water. A pressure sensor 350 is attached to the other end of the liquid-filled tube 355. The pressure read from pressure sensor is used to determine the vertical height, H, of the pressure sensor 350 as above (P=ρH). Thus, when the pressure sensor 360 is placed on the optical device 328, and the optical device 328 is positioned at the "highest position", then the pressure reading from the pressure sensor 350 may be used to determine the height from the reference point to the highest position along the jugular vein to yield an output signal.

The central venous pressure may also be determined utilizing pressure detection e.g. determination of a pressure waveform, as described above and an externally applied pressure. In this case, a pressure waveform is obtained, as described, and monitored via a display unit 44. An external pressure is then applied to the selected venous vessel from the skin surface while monitoring the pressure waveform (representative of baseline pressure). The externally applied pressure is increased until the pressure waveform disappears as determined by monitoring the display unit. The central venous pressure $P_c$ is then determined as follows:

$$P_c = P_{ef} - P_{ei}$$

wherein $p_{ef}$ is the value of the externally applied pressure at which the pressure waveform disappears and $p_{ei}$, is the value of pressure at which the pressure waveform starts to change (or the amplitude of the waveform starts to decrease).

A device comprising two light source-detector pairs, or two patches each comprising a light source-detector pair may be used in accordance with the foregoing method.

Central venous blood flow velocity may also be measured using a device in accordance with the present invention. By measuring the rise or fall time of a pressure waveform (t), or the mean of the rise and fall time, the central venous blood flow can be calculated as follows:

$$v = \frac{d}{t}$$

wherein d is the spacing between the source and photodetector; and
t is the rise time of the pressure waveform (from the bottom to the peak).

The blood flow may be estimated according to:

$$F = v \times S$$

wherein S is the cross-sectional area of the blood vessel, which can be obtained through ultrasound imaging, and velocity (v) is determined as indicated above.

In a further embodiment of the present invention, a device corresponding to the device of FIG. 1 is provided which is adapted to generate an output from a cardiac vein remotely. Accordingly, the device comprises a remote light source capable of delivering a light beam to a desired site on a patient, e.g. a site on the neck of the patient in close proximity to a cardiac vessel; and a remote photodetector, such as a CCD camera adapted to receive light from the source which is reflected off of the patient at the desired site. As described, the photodetector generates an output signal (e.g. current/voltage) that may be processed by a signal-processing device to generate a visual output (e.g. waveform) for display on a display unit.

Embodiments of the present invention are described by reference to the following specific examples which are not to be construed as limiting.

Example 1—Measurement of Venous Pulse in a Patient

Figure 12:
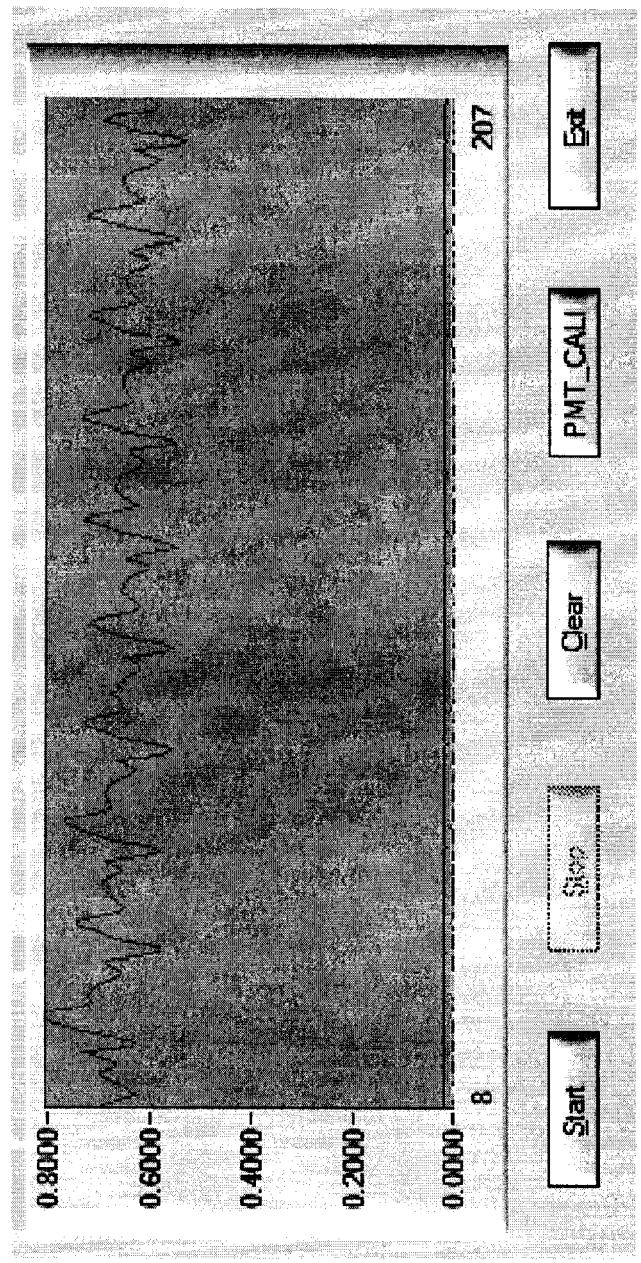
FIG. 12 illustrates a waveform obtained using a device in accordance with the invention.

The venous pulse of a human subject was obtained using a device as shown in FIG. 1. The patient lay on a chair at about a 30 degree recline. The sensor patch of the device was placed on the neck of the patient at a site over the internal jugular vein. While the subject maintained normal breathing, venous pulse was measured and recorded. FIG. 12 illustrates the waveform recorded. The amplitude of the detected signal is represented along the y-axis while the x-axis represents time.

Example 2—Measurement of Central Venous Pressure in a Patient

Figure 15:
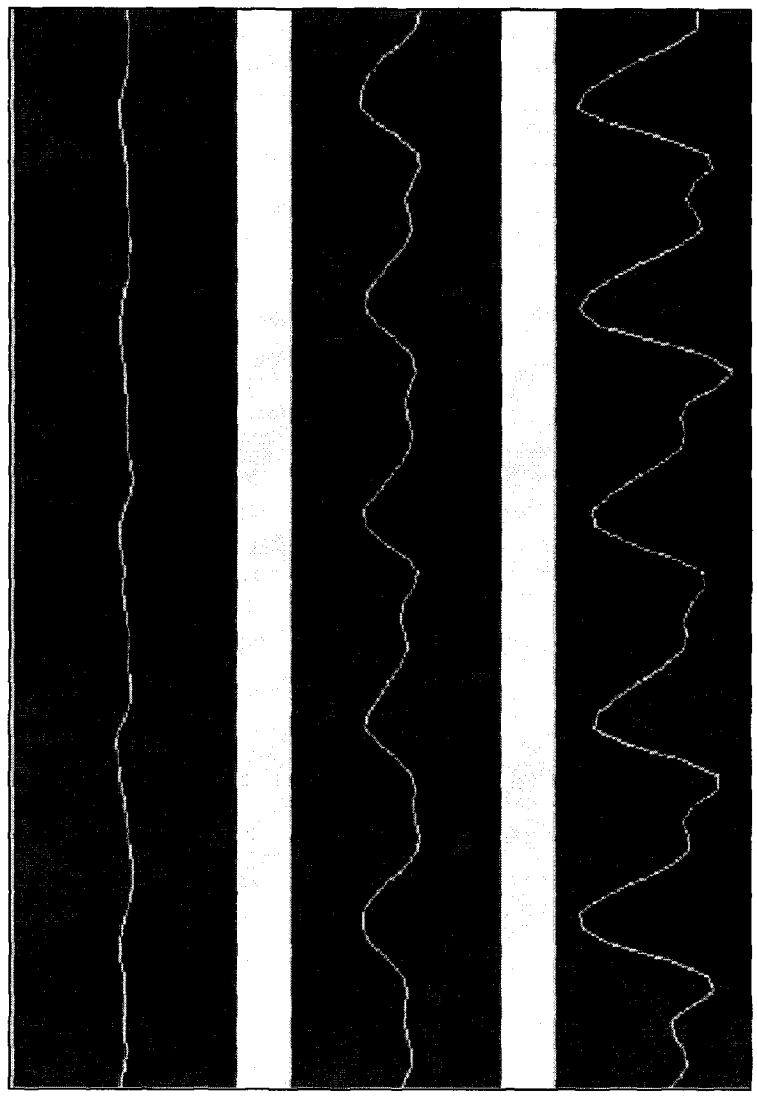
FIG. 15 illustrates a waveform obtained using a device according to FIG. 13 (B) in three different positions (A)

The central venous pressure of a human subject was obtained using a device as shown in FIG. 13. The sensor patch of the device was placed on the neck of the patient at a site over the internal jugular vein such that the terminal source/detector of the device was at the sternal angle of the subject. While the subject maintained normal breathing, venous pressure was measured and recorded as a function of body position when the patient was lying flat (0 degree incline, e.g. horizontal), at a partial rise (45 degree incline from the horizontal) and sitting upright (90 degree incline from the horizontal) as shown in FIG. 15A. The measured pressure as depicted by the waveform illustrated in FIG. 15B is consistent with the expected central venous pressure in a healthy subject which decreases as body position rises from the horizontal position.

Example 3—Use of a Device with Pressure Sensor to Measure Patient CVP

A simulated patient system was developed to test a height sensor device 360 as shown in FIG. 18. The simulation (as shown in FIG. 19) included a cylindrical tissue phantom representing the patient's neck in which a tube 410 representing the jugular vein was embedded. A corresponding tube 412, joined at a T-junction to the jugular vein tube 410, represented a CVP catheter and was used to illustrate the height of fluid in the jugular vein. The fluid used in the system was water. A single tube extended downwardly from the T-junction and connected to a rubber "heart". The heart is connected to a rotation pump which accurately simulates heart beats within the heart and pumps water through the system.

An optical sensor device with LED and photo detectors 328 (as in FIG. 13) was placed on the surface of the tissue phantom at a position that was over the simulated "jugular vein". A pressure sensor 350 was placed on top of the optical sensor device, and the tube 355 extending from the pressure sensor was attached to a moveable bar on a digital ruler. The moveable bar was positioned to be at a "reference point" for CVP measurement, e.g. zero reference is the phlebostatic axis (which approximates the location of the right atrium).

The device according to FIG. 18 was used to non-invasively measure the CVP of the simulated patient. CVP is clinically defined as the vertical height of fluid in the jugular vein relative to the zero reference. When the optical sensor was determined to be at the highest position (e.g. by monitoring the output of the optical sensor as previously described), the pressure reading from the pressure sensor at this position was used to determine the height of the optical sensor (i.e. the highest position) relative to the reference. The pressure read from the pressure sensor was then used to determine the vertical height, H, of the pressure sensor according to P=pH.

The height/CVP "non-invasively" obtained using the optical and pressure sensing devices was confirmed by comparison with the actual height value obtained using the digital ruler. The moveable bar of the digital ruler was moved to the top of the liquid in the simulated "catheter" tube. The height measurement obtained using the digital ruler was comparable to the value obtained using the devices as above indicating that the optical and pressure sensing devices accurately measured CVP in the simulated patient.

Example 4—Measurement of Venous Blood Oxygenation

A probe having two detectors and a light source is used to determine venous blood oxygenation. The detectors of the probe were located at different distances from the light source. The first detector, D1, was spaced 2 cm from the light source, while the second detector, D2, was spaced 2.5 cm from the light source as shown in FIG. 19. The light source emitted two wavelengths of light, 660 nm and 880 nm.

The probe was placed on a patient's neck at the vicinity of the internal jugular vein, and signal amplitude of 660 nm and 880 nm light beams was measured at detector 2 and detector 1, respectively. These values were then used to calculate the attenuation factor (AF) of tissue to each wavelength:

$$AF\_660 \text{ nm} = D2\_660 \text{ nm}/D1\_660 \text{ nm}$$

$$AF\_880 \text{ nm} = D2\_880 \text{ nm}/D1\_880 \text{ nm}$$

The attenuation correction factor (C) was then calculated based on the ratio of AF at 660 nm and 880 nm, i.e. (C=AF_660 nm/AF_880 nm).

Using the probe, venous blood oxygenation corrected based on the attenuation correction factor ($S_{jv}O_2$(corrected)=A+B*(C*R)) was determined. A and B constants for this probe were determined to be: A=1.11, B=−0.27.

The corrected venous blood oxygenation was compared to the actual value obtained by invasive methods and found to correlate well, while the uncorrected value of venous blood oxygenation differed significantly from the actual value by up to about 20%.

REFERENCES

1. Naveen Greg et al, "Jugular Venous Pulse: An Appraisal", Journal, Indian Academy of Clinical Medicine, Vol 1, No. 3, October-December, 2000
2. Reference: O'Rourke, R. A. and Others, General Examination of the Patient, Hurst's, The Heart, Eighth Edition, Pp. 238-242
3. http://depts.washington.edu/physdx/neck/tech2.html
4. Conway "Clinical assessment of cardiac output", Eur. Heart J. 11, 148-150 (1990).
5. "Advances in non-invasive cardiac output monitoring", Annals of Cardiac Anaesthesia, 2002, volume 5, p 141-148.
6. "Thermodilution method for measuring cardiac output", Europ. Heart J. 11(Suppl 1), 17-20, 1990.
7. "The dye dilution method for measurement of cardiac output", Europ. Heart J. 11 (Suppl 1), 6-12 (1990))
8. de Leeuw and Birkenhager ("Some comments of the usefulness of measuring cardiac output by dye dilution", Europ. Heart J. 11 (Suppl 1), 13-16 (1990)).
9. "Continuous measurement of cardiac output by the Fick principle: Clinical validation in intensive care", Crit Care Med 20(3), 360-365 (1992)
10. Doi et al., "Frequently repeated Fick cardiac output measurements during anesthesia", J. Clin. Monit. 6, 107-112 (1990).
11. "Measurement of cardiac output before and after cardiopulmonary bypass: Comparison among aortic transit-time ultrasound, thermodilution, and noninvasive partial CO2 rebreathing", J. Cardiothoracic. Vasc. Anesth. 18(5) 563-572 (2004).
12. Nielsson et al. al "Lack of agreement between thermodilution and CO2-rebreathing cardiac output" Acta Anaesthesiol Scand 2001; 45:680.
13. Schmidlin et al, "Transoesophageal echocardiography in cardiac and vascular surgery: implications and observer variability", Brit. J. Anaesth. 86(4), 497-505 (2001).
14. Manning et al. "Validity and reliability of diastolic pulse contour analysis (Windkessel model) in humans", Hypertension. 2002 May; 39(5):963-8.
15. "Pulse contour analysis versus thermodilution in cardiac surgery", Acta Anaesthesiol Scand 2002; 46:424, Linton et al.
16. "Estimation of changes in cardiac output from arterial blood pressure waveform in the upper limb", Br J Anaesth 2001; 86:486 and Jansen et al.
17. "A comparison of cardiac output derived from the arterial pressure wave against thermodilution in cardiac surgery patients" Br J Anaesth 2001; 87:212.
18. Jansen et al. "An adequate strategy for the thermodilution technique in patients during mechanical ventilation", Intensive Care Med 1990; 16:422.

I claim:

1. A device comprising:
   at least one light source adapted to emit light in the 400 nm to 1000 nm wavelength range;
   at least one photodetector adapted to receive light emitted by the light source and translate said light into a recordable output wherein said light is reflected from or transmitted through tissue of the patient;
   at least one probe which facilitates delivery of light from the light source to an external tissue site on the patient in the proximity of the jugular vein and receipt of light reflected from or transmitted through said patient site by the photodetector;
   a pressure sensor mounted on the probe and connected to a reference patch that is compatible for placement on the skin via a tube configured to contain a liquid, wherein the pressure sensor provides a pressure reading useful to determine vertical height from the reference patch to the probe; and
   a signal processing means adapted to receive the photodetector output and the pressure reading from the pressure sensor and to calculate a central venous pressure therefrom.

2. The device as defined in claim 1, wherein said light source and said photodetector are embedded in said probe.

3. The device as defined in claim 1, comprising a plurality of photodetectors.

4. The device as defined in claim 3, comprising a plurality of light sources, wherein each light source emits light that is received by a corresponding photodetector of said plurality of photodetectors.

5. The device as defined in claim 1, comprising a plurality of probes, wherein each probe comprises at least one light source and at least one photodetector.

6. The device as defined in claim 1, wherein the recordable output is current or voltage.

* * * * *